United States Patent [19]
Choi et al.

[11] Patent Number: 5,498,599
[45] Date of Patent: Mar. 12, 1996

[54] METHODS FOR STIMULATING PLATELET PRODUCTION

[75] Inventors: Esther S. Choi, Santa Barbara; Martha M. Hokom, Thousand Oaks; Pamela Hunt, Thousand Oaks; Janet L. Nichol, Oxnard, all of Calif.

[73] Assignee: AMGEN Inc., Thousand Oaks, Calif.

[21] Appl. No.: 184,327

[22] Filed: Jan. 21, 1994

[51] Int. Cl.$^6$ .......................... C12N 15/18; C12N 15/19; A61K 38/18; A61K 38/19
[52] U.S. Cl. ................. 514/12; 514/2; 514/814; 514/833; 514/885
[58] Field of Search ................ 435/69.1, 240.2, 435/320.1; 514/2, 12, 814, 833, 885; 530/350, 351, 399

[56] References Cited

U.S. PATENT DOCUMENTS

| | | | |
|---|---|---|---|
| 5,032,396 | 7/1991 | Williams | 424/85.2 |
| 5,087,448 | 2/1992 | Burstein | 424/85.2 |
| 5,128,449 | 7/1992 | McDonald | 530/351 |
| 5,180,678 | 1/1993 | Druez et al. | 436/501 |
| 5,198,356 | 3/1993 | Lieberman et al. | 435/240.2 |

FOREIGN PATENT DOCUMENTS

| | | |
|---|---|---|
| WO93/13132 | 7/1993 | Japan. |
| 92/07074 | 4/1992 | WIPO. |

OTHER PUBLICATIONS

Narazaki, M., et al., Blood 82(4):1120–1126 (1993).
Williams, N. and Levine, R. F., British Journal of Haematology 52:173–180 (1982).
Levin, J., Molecular Biology and Differentiation of Megakaryocytes, Pub. Wiley–Liss, Inc.: 1–10 (1990).
Geewirtz, A. M., The Biology of Hematopoiesis, pub. Wiley–Liss, Inc.: 123–132 (1990).
Han, Z. C., et al., Int. J. Hematol. 54:3–14 (1991).
Nieuwenhuis, H. K. and Sixma, J. J., New Eng. J. of Med. 327:1812–1813 (1992).
Long, M., Stem Cells 11:33–40 (1993).
Hoffman, R., et al., Blood Cells 13:75–86 (1987).
Murphy, M. J., Hematology/Oncology Clinics of No. America 3(3):465–478 (1989).
Hoffman, R., Blood 74 (4):1196–1212 (1989).
Mazur, E. M. and Cohen, J. L., Clin. Pharmacal Ther. 46(3):250–256 (1989).
Gewirtz, A. M. and Calabretta, B., Int. J. Cell Cloning 8:267–276 (1990).
Williams, N., Progress in Growth Factor Research 2:81–95 (1990).
Gordon, M. S. and Hoffman, R., Blood 80 (2):302–307 (1992).
Hunt, P. et al., Exp. Hematol. 21:372–381 (1993).
Hunt, P. et al., Exp. Hematol.21:1295–1304 (1993).
Wendling, F., et al. Leukemia 3(7):475–480 (1989).
Wendling, F., et al. Blood 73(5):1161–1167 (1989).
Souyri, M., et al. Cell 63:1137–1147 (1990).
Vigon, I., et al. Proc. Natl. Acad. Sci. USA 89:5640–5644 (1992).
Skoda, R. C., et al. The EMBO Journal 12(7):2645–2653 (1993).
Ogawa, Makio, Blood 81 (11):2844–2853 (1993).
Methia, N., et al. Blood 82 (5):1395–1401 (1993).
Wendling, F., et al. Blood 80:246a.
Vigon, I., et al. Oncogene 8:2607–2615 (1993).

*Primary Examiner*—Marianne P. Allen
*Attorney, Agent, or Firm*—Robert R. Cook

[57] ABSTRACT

Disclosed is a method for increasing the number of platelets in a mammal, which comprises administering to the mammal a platelet number increasing effective amount of an unbound, preferably a soluble, MPL receptor.

6 Claims, 6 Drawing Sheets

METHODS FOR STIMULATING PLATELET PRODUCTION

FIELD OF THE INVENTION

The present invention relates to the stimulation and growth of cells, particularly megakaryocytes and platelets, and specifically to the use of the so-called MPL receptor as an inducer of megakaryocyte differentiation into platelets. The present invention also relates to compositions capable of bringing about such platelet production in vivo.

BACKGROUND OF THE INVENTION

At least two broad areas of research are involved in the present invention. The first relates to the development and production of platelets from megakaryocytes and the second relates to a polypeptide member of a growth factor receptor family, referred to herein as the MPL receptor. Each of these areas of research will now be outlined in the following.

A. Platelet Production From Megakaryocytes

Blood platelets are circulating cells that are crucial for the prevention of bleeding and for blood coagulation. Megakaryocytes are the cellular source of platelets and arise from a common bone marrow precursor cell which gives rise to all hematopoietic cell lineages. This common precursor cell is known as the pluripotent stem cell or PPSC.

A hierarchy of megakaryocytic progenitor cells has been defined based on the time of appearance and size of megakaryocyte (MK) colonies appearing in in vitro culture systems in response to appropriate growth factors. The burst-forming unit megakaryocyte (BFU-MK) is the most primitive megakaryocyte progenitor cell. BFU-MK are thought to ultimately produce numerous colony forming unit megakaryocytes (CFU-MK), which are more differentiated MK progenitor cells.

As the MK undergo subsequent differentiation, MK cells lose the ability to undergo mitosis but acquire an ability to endoreduplicate. Endoreduplication is the phenomenon in cells of nuclear division in the absence of cell division. Endoreduplication ultimately results in an MK which is polyploid. Further MK maturation results in acquisition of cytoplasmic organelles and membrane constituents that characterize platelets.

Platelets are produced from mature MK's by a poorly defined process that has been suggested to be a consequence of MK physical fragmentation, or other mechanisms. Observations of extensive membranous structures within megakaryocytes has led to a model of platelet formation in which a demarcation membrane system outlines nascent platelets within the cell body. Another model of platelet formation has developed from observations that megakaryocytes will form long cytoplasmic processes constricted at platelet-sized intervals from which platelets presumably break off due to blood flow pressures in the marrow and/or in the lung. These cytoplasmic processes were termed proplatelets by Becker and DeBruyn to reflect their presumed precursor role in platelet formation. See Becker and DeBruyn, *Amer. J. Anat.* 145:183 (1976).

FIG. 1 presents an overview of the various precursor cells involved in megakaryocyte and platelet development. The cell at the far left-hand side of the figure may be considered a PPSC, and the additional cells to the right of the PPSC in the figure may be thought of as BFU-MK, followed by CFU-MK. The cell that is undergoing endomitosis, which is located immediately to the right of the PPSC in the figure, is a mature megakaryocyte cell. As a result of endomitosis, this cell has become polyploid. The next structure to the right includes the long cytoplasmic processes that are constricted at platelet-sized intervals emerging from the polyploid nucleus of the mature megakaryocyte cell. In the far right-hand side of the figure are shown a number of platelets that have been produced by fragmentation of the cytoplasmic processes in the immediately preceding megakaryocyte cell.

The following is a summary of some prior publications relating to the above description of megakaryocyte maturation and the production of platelets:

1. Williams, N. and Levine, R. F., *British Journal of Haematology* 52:173–180 (1982).

2. Levin, J., *Molecular Biology and Differentiation of Megakaryocytes*, pub. Wiley-Liss, Inc.: 1–10 (1990).

3. Gewirtz, A. M., *The Biology of Hematopoiesis*, pub. Wiley-Liss, Inc.: 123–132 (1990).

4. Han, Z. C., et al., *Int. J. Hematol.* 54:3–14 (1991).

5. Nieuwenhuis, H. K. and Sixma, J., *New Eng. J. of Med.* 327:1812–1813 (1992).

6. Long, M., *Stem Cells* 11:33–40 (1993).

B. Regulation Of Platelet Formation

A large body of data generated in many laboratories indicates that platelet production is regulated by humoral factors. The complexity of this biological process was not originally appreciated and currently it appears that a number of human growth factors possess this capability.

Megakaryocyte regulation occurs at multiple cellular levels. A number of cytokine cell proliferation factors amplify platelet production by expanding the progenitor cell pool. A second group of humoral growth factors serves as maturation factors acting on more differentiated cells to promote endoreduplication. In addition, there appear to be two independent biofeedback loops regulating these processes.

Several lineage nonspecific hematopoietic growth factors exert an important effect on MK maturation. Granulocyte-macrophage colony stimulating factor (GM-CSF), interleukin-3 (IL-3), IL-6, IL-11, leukemia inhibitory factor (LIF), and erythropoietin (EPO) each individually promote human MK maturation in vitro as determined by their effects on MK size, number, or ploidy. The MK maturational effects of LIF, IL-6, and IL-11 are either partially (LIF and IL-6) or totally (IL-11) additive to those of IL-3. Such data suggest that combinations of cytokines may be necessary to promote MK maturation in vivo.

The following is a summary of some prior publications relating to the regulation of megakaryocyte and platelet production:

7. Hoffman, R. et al., *Blood Cells* 13:75–86 (1987).

8. Murphy, M. J., *Hematology/Oncology Clinics of North America* 3 (3):465–478 (1988).

9. Hoffman, R., *Blood* 74 (4):1196–1212 (1989).

10. Mazur, E. M. and Cohen, J. L., *Clin. Pharmacol. Ther.*, 46 (3):250–256 (1989).

11. Gewirtz, A. M. and Calabretta, B., *Int. J. Cell Cloning* 8:267–276 (1990).

12. Williams, N., *Progress in Growth Factor Research* 2:81–95 (1990).

13. Gordon, M. S. and Hoffman, R., *Blood* 80 (2):302–307 (1992).

14. Hunt, P. et al., *Exp. Hematol.* 21:372–281 (1993).

15. Hunt, P. et al., *Exp. Hematol.* 21:1295–1304 (1993).

C. The MPL Receptor

The myeloproliferative leukemia virus (MPLV) is a murine replication-defective retrovirus that causes acute leukemia in infected mammals. It has been discovered that a gene expressed by MPLV consists of a part of the gene that encodes the retroviral envelope (or external protein coat) of the virus fused to a sequence that is related to the cytokine receptor family, including the receptors for GM-CSF, G-CSF, and EPO.

Expression of the MPLV gene described above has the interesting biological property of causing murine progenitor cells of various types to immediately acquire growth factor independence for both proliferation and terminal maturation. Moreover, some cultures of bone marrow cells acutely transformed by MPLV contained megakaryocytes, suggesting a connection between the MPLV gene and megakaryocyte growth and differentiation.

It is now recognized that the MPLV viral gene (referred to as v-MPL) has a homolog in mammalian cells, which is referred to as a cellular MPL gene (or c-MPL). Using v-MPL-derived probes, a cDNA corresponding to the human c-MPL gene was cloned. See PCT published application WO 92/07074 (published Apr. 30, 1992; discussed below). Sequence analysis has shown that the protein encoded by the c-MPL gene product belongs to the highly conserved cytokine receptor superfamily, just like the homologous v-MPL gene product.

This cellular gene, c-MPL, is thought to play a functional role in hematopoiesis based on the observation that its expression was found in bone marrow, spleen, and fetal liver from normal mice by Northern blot analysis, but not in other tissues. In particular, c-MPL is expressed on megakaryocytes. It has also been shown that the human cellular gene, human c-MPL, is expressed in purified megakaryocytes, platelets and other cells that express the CD34 antigen, which is indicative of early hematopoietic progenitor cells. Furthermore, exposure of CD34 positive cells to synthetic oligodeoxynucleotides that are anti-sense to the c-MPL mRNA or message significantly inhibits the colony forming ability of CFU-MK megakaryocyte progenitors, but has no effect on erythroid or granulomacrophage progenitors.

In total, the above data and observations suggest that the c-MPL-encoded protein could be the receptor for a cytokine specific for regulating megakaryocytopoiesis. In other words, c-MPL appears to encode a cell surface receptor, referred to herein as the MPL receptor, that binds to a ligand, which activates the receptor, possibly leading to production of megakaryocytes.

PCT patent publication WO 92/07074 is directed to the sequence of the protein produced by the c-MPL gene, from both human and murine sources. This gene product, which is thought to be a receptor as explained above, is made up of at least three general regions or domains: an extracellular domain, a transmembrane domain, and an intracellular (or cytoplasmic) domain. Attached together, these domains make up the intact MPL receptor. This PCT publication also refers to a soluble form of the receptor that substantially corresponds to the extracellular domain of the mature c-MPL protein. The intracellular domain contains a hydrophobic region that, when attached via the transmembrane region to the extracellular domain of the protein, renders the overall protein subject to aggregation and insolubility. On the other hand, when the extracellular domain of the c-MPL gene product is separated from the transmembrane domain and the intracellular domain, it becomes soluble, hence the extracellular form of the protein is referred to as a "soluble" form of the receptor.

A number of researchers are currently pursuing the isolation and characterization of the putative ligand which binds specifically to the c-MPL receptor. It is expected that such ligand will stimulate the production of mature megakaryocytes and/or platelets. To date, however, no one has reported the purification or final structure of such a ligand. On the other hand, according to the prior publications relating to the MPL receptor (i.e., the intact c-MPL gene product), the soluble form of the MPL receptor would be expected to bind to circulating free MPL ligand, thus inhibiting the formation of megakaryocytes and/or platelets.

The following is a summary of some prior publications relating to the above description of the v-MPL and c-MPL receptors and genes:

16. Wendling, F., et al., *Leukemia* 3 (7):475–480 (1989).

17. Wendling, F., et al., *Blood* 73 (5):1161–1167 (1989).

18. Souyri, M., et al., *Cell* 63:1137–1147 (1990).

19. Vigon, I., et al., *Proc. Natl. Acad. Sci.* U.S.A. 89:5640–5644 (1992).

20. Skoda, R. C., et al., *The EMBO Journal* 12 (7):2645–2653 (1993).

21. Ogawa, M. *Blood* 81 (11):2844–2853 (1993).

22. Methia, N., et al., *Blood* 82 (5):1395–1401 (1993).

23. Wendling, F, et al., *Blood* 80:246a (1993).

D. The Need For An Agent Capable Of Stimulating Platelet Production

It has been reported recently that platelet transfusions are being administered at an ever increasing rate at medical centers in North America, Western Europe, and Japan. See Gordon, M. S. and Hoffman, R., *Blood* 80 (2):302–307 (1992). This increase appears to be due in large measure to advances in medical technology and greater access to such technologies as cardiac surgery and bone marrow, heart, and liver transplantation. Dose intensification as a means of delivering therapies to cancer patients and the HIV-1 epidemic have also contributed to the heavy demand on the platelet supply.

Platelet usage carries with it the possibility of transmission of the many blood-born infectious diseases as well as alloimmunization. Moreover, the production of purified platelets is an expensive endeavor and hence the increasing use of such platelets increases overall medical costs. As a result, there exists an acute need for new and improved methods for producing platelets for human uses.

Exemplary prior approaches to enhancing platelet production are described in the following:

U.S. Pat. No. 5,032,396 reports that interleukin-7 (IL-7) is capable of stimulating platelet production. Interleukin-7 is also known as lymphopoietin-1 and is a lymphopoietic growth factor capable of stimulating growth of B- and T-cell progenitors in bone marrow. Published PCT application Ser. No. 88/03747, filed Oct. 19, 1988 and European patent application number 88309977.2, filed Oct. 24, 1988 disclose DNA's, vectors, and related processes for producing mammalian IL-7 proteins by recombinant DNA technology. The data presented in the U.S. patent show that IL-7 can increase circulating platelets in normal and sublethally irradiated mice.

U.S. Pat. No. 5,087,448 discloses that megakaryocytes and platelets can be stimulated to proliferate in mammals by treating them with interleukin-6. Recombinant human interleukin-6 is a 26,000 molecular weight glycoprotein with multiple biological activities. The data presented in this patent show that IL-6 has an effect of increasing colonies of megakaryocytes in vitro.

Neither of the above-cited patents mentions anything with respect to the MPL receptor, which is involved in the present invention.

In spite of the above disclosures, there remains a strong need for new stimulators of megakaryocytes and/or platelets in mammals.

SUMMARY OF THE INVENTION

It is an object of the present invention to provide a means of stimulating production of megakaryocytes and/or platelets in vivo in a mammal in need thereof.

It is another object of the present invention to provide a treatment for platelet deficiencies in mammals, such as a human in need of such treatment.

It is yet another object of the present invention to provide compositions for treating platelet deficiencies in mammals, such as humans.

These and other objects of the present invention as will hereinafter be described in greater detail, have been achieved by the discovery by the present inventors that administration of an unbound MPL receptor (defined below) to a mammal, results in an increased number of platelets in such mammal. The present invention also provides compositions for inducing platelet production, comprising an effective quantity of an unbound MPL receptor in admixture with one or more pharmaceutically acceptable diluents, carriers or excipients, as well as methods of using an unbound MPL receptor to prepare pharmaceutical compositions for inducing and enhancing platelet production in mammals.

BRIEF DESCRIPTION OF THE FIGURES

Numerous features and advantages of the present invention will become apparent upon review of the figures, wherein.

DETAILED DESCRIPTION OF THE INVENTION

Figure 1:
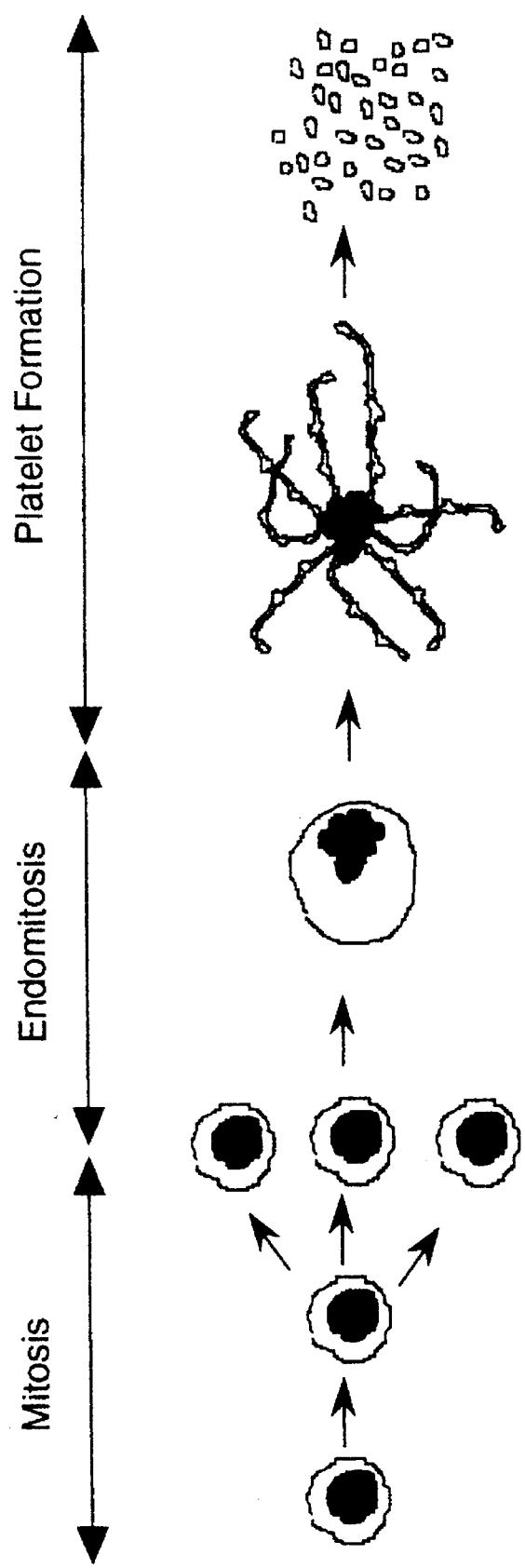
FIG. 1 depicts an overview of development and maturation of megakaryocytes and platelets.

Additional aspects and advantages of the invention will be apparent to those skilled in the art upon consideration of the following detailed description, which details the practice of the invention.

The present invention is based on the unexpected discovery that MPL receptor, in unbound form, is capable of stimulating an increase in the number of platelets in vivo in mammals. This is believed to be due to an increased rate of megakaryocyte fragmentation into platelets. While it was previously appreciated that the MPL receptor might have some involvement in megakaryo-cytopoiesis, the understanding in the art was that when the receptor was bound to a megakaryocyte cell, it required stimulation by a ligand to cause the megakaryocyte to mature and/or to produce platelets. Based on the above hypothesis, it was a logical expectation that MPL receptor not attached to a cell surface (i.e., "unbound MPL receptor") would compete for ligand with the MPL receptor bound to the cell, thereby removing ligand that would normally stimulate the cell to produce megakaryocytes and platelets, with the final effect being fewer cells proceeding to produce megakaryocytes and platelets.

The present inventors, however, have discovered that the Opposite of the above-described expected result is actually observed. That is, in in vivo experiments in mammals, unbound MPL receptor has the effect of enhancing the production of megakaryocytes and platelets.

While not wishing to be bound by any particular mechanism or theory of action, the present inventors have formulated a hypothesis which may explain the effects described herein. This hypothesis is that the ligand that normally stimulates the bound MPL receptor produces mature megakaryocytes from less mature cells (e.g., PPSC, BFU-MK, CFU-MK), but that once these mature megakaryocytes are produced, in order to proceed to form proplatelets, the ligand must be removed. If the ligand is not removed from the mature megakaryocyte, this megakaryocyte remains in the mature form rather than producing platelets.

Using the above hypothesis as a model, the administration of unbound MPL receptor would serve to allow mature megakaryocytes to proceed to form proplatelets and then fragment into platelets. At the same time, removal of the MPL ligand by the unbound MPL receptor may also inhibit the formation of additional mature megakaryocytes. If this hypothetical model is correct, it leads to the conclusion that even greater platelet formation might be achieved upon administration of both the ligand and the unbound MPL receptor, since such administration would result in both enhanced production of mature megakaryocytes as well as stimulation of the production of platelets from the mature megakaryocytes. Sequential administration of ligand followed by unbound receptor might even further enhance the effect. In any case, the present inventors believe that this discovery is completely unexpected in view of the prior models of platelet formation and MPL receptor/ligand activity.

DEFINITIONS

The following definitions explain the meaning of key terms and phrases in the claims herein.

By "increasing the number of platelets" is meant that the number of platelets is significantly elevated above the normal range of platelets in the particular mammal involved. The elevation of platelet counts may occur in a time-dependent manner, and may be cyclical, increasing and then constant or decreasing, or constant, etc.

Figure 4:
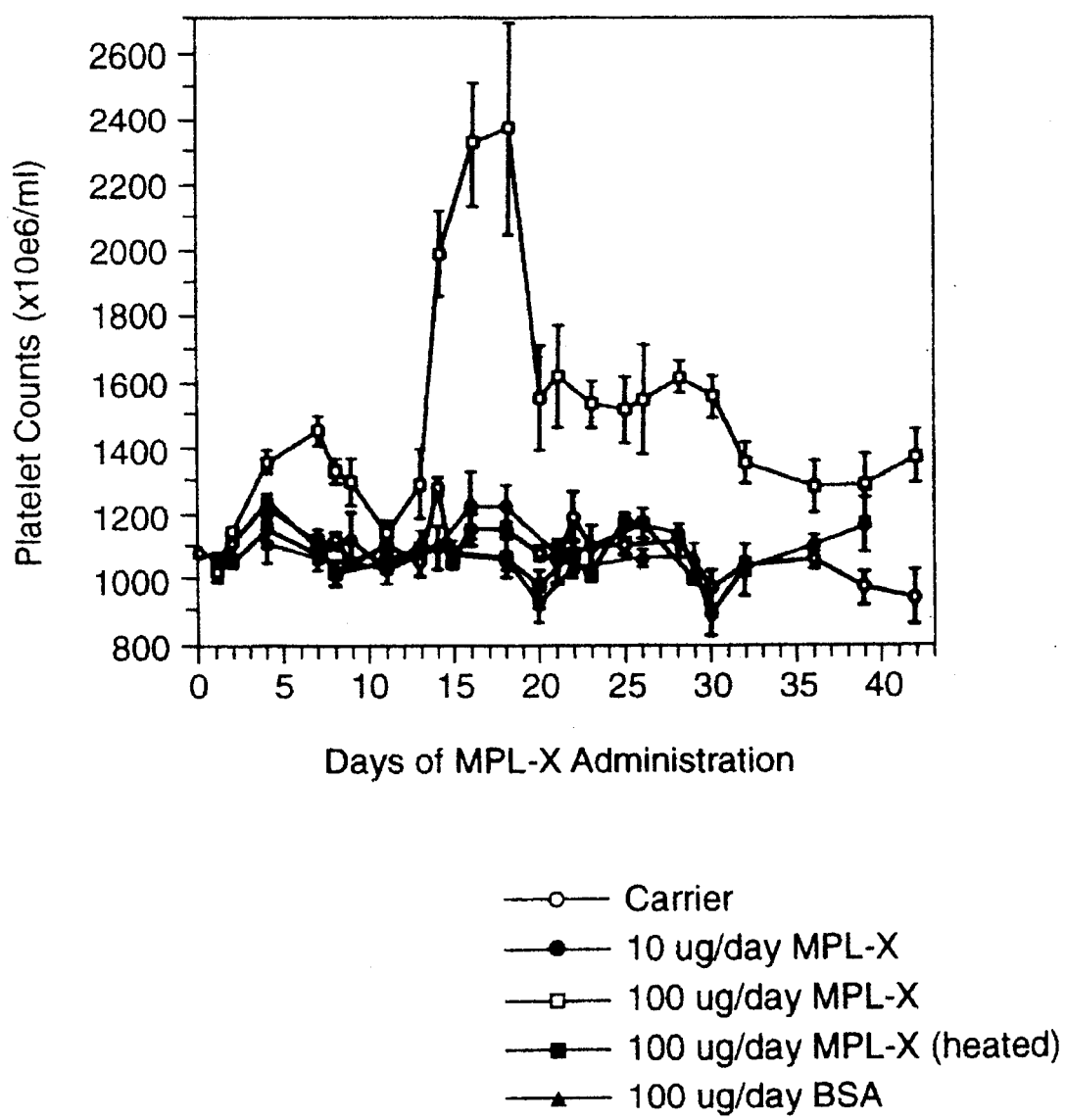
FIG. 4 presents data showing the effect of MPL-X in vivo on platelet counts in a mouse model.

For example, with reference to FIG. 4, it appears that there are at least three cycles of elevated platelet count, with the first occurring at about seven to eight days, the second and more enhanced cycle occurring at between nineteen and twenty days, and the third cycle occurring at about twenty-eight to twenty-nine days. These cycles occurred in several mice in a particular model system, and may or may not be duplicated in other mammalian systems or models.

Preferably, the elevation in platelet count will be at least about forty to fifty percent above the average of the normal range, but may be considerably higher, such as up to about a two-fold increase as compared to the normal average number of platelets. It should be born in mind that any significant increase, such as, for example, five to ten percent, might be clinically sufficient in a given situation. The increase in platelet count is a function of, among other variables, the dose of the unbound MPL receptor administered to the mammal, and so can be altered over a wide range.

Platelets may be counted by any of various standard methods. One exemplary method involves the use of a commercially available blood cell counter. Such instruments "count" particles and classify them into cell types based essentially on size. Instruments such as the Sysmex or the Coulter Counter are exemplary. For a discussion of such methods, see Bloom, A. L. and Thomas, D. P. (eds.), *Haemostasis and Thrombosis* (Second Edition) Churchill Livingstone: 936 (1987).

The "mammal" to be treated is not specifically limited, but is preferably a human. Other mammals that might be treated include dogs, cats, cows, horses, etc. Cross-species activity (i.e., activity of an MPL receptor from one species in another species) is also expected, especially if there is a high (e.g., equal to or above around 80%) homology between the MPL receptors from the two species, and is therefor another aspect of the present invention. For example, murine unbound MPL receptor could be used to increase the number of platelets in a human. However, it is expected that the greatest activity will be achieved using the same species' MPL receptor as the species being treated.

"Administration" may be carried out by any convenient method. For example, bolus injection, continuous infusion, sustained release from implants, or any other suitable technique could be used. Intravenous administration is preferred. Multiple administrations of unbound MPL receptor are also contemplated.

A "platelet number increasing effective amount" is an amount sufficient to significantly raise the number of platelets in a particular mammal. If necessary or desired, this amount can be appropriately determined in preliminary trials, without undue experimentation, and depending upon the level of increase desired in the mammal being treated. Generally, doses of 1 μg to 100 μg per kilogram per day, preferably 10 μg to 100 μg per kilogram per day for one to twenty days can be expected to induce a therapeutically significant biological effect. The unbound MPL receptor may be administered each day for a period of days, all at once on a first day followed by one or more days without administration, etc. Preferably, bolus injections of 10 μg per kilogram per day can be given at 3-day intervals as a stimulator of platelet production.

In addition to the unbound MPL receptor, one or more additional lymphokines or cytokines may be administered simultaneously or sequentially with the MPL receptors of the present invention. Such lymphokines and/or cytokines may be, for example, IL-1 alpha, IL-1 beta, IL-2, IL-3, IL-4, IL-5, IL-6, IL-11, colony stimulating factor-1 (CSF-1), GM-CSF, granulocyte colony stimulating factor (G-CSF), EPO, interferon-alpha (IFN-alpha), IFN-beta, or IFN-gamma. It is also possible to include the MPL ligand once it is available. Any of these may work additively or synergistically with the unbound MPL receptors.

By "unbound MPL receptor" is meant an MPL receptor molecule that is free from the ordinary cellular constituents, especially the cell membrane. Preferably, the unbound receptor will be the so-called "soluble" form of the receptor. The "soluble" form of the MPL receptor may be any such form known to or subsequently developed by those skilled in the art. Generally, the soluble form of the receptor will be one which substantially lacks the transmembrane domain of the receptor molecule.

It is known that the transmembrane domain of the MPL receptor is very hydrophobic, and therefore it is highly preferred that substantially all of this domain of the MPL receptor be removed for purposes of this invention. Although the intracellular domain of the MPL receptor is not considered insoluble, it is nevertheless preferred that this domain also be substantially removed from the MPL receptor for purposes of this invention.

In summary, by "soluble" is meant that the material is not bound to a cell, and preferably includes substantially none (i.e., fewer than about 10 residues) of the transmembrane or intracellular domains of the full-length molecule. The soluble MPL receptor (which is also referred to herein as MPL-X) is capable of being dissolved in aqueous solution as well as body fluids, such as blood, serum, saliva, cerebrospinal fluid, urine, etc. It is also possible to use the extracellular domain of the MPL receptor directly attached to the intracellular domain of the receptor. As used herein, "MPL receptor" preferably refers to the cellular form of this receptor (i.e., the c-MPL gene product) rather than the virally-derived form of the gene (i.e., v-MPL).

The intact MPL receptor and its constituent domains are described in detail in published PCT publication WO92/07074, published Apr. 30, 1992. Further details on the murine form of the MPL receptor are found in Vigon, et al., *EMBO* 8:2607–2615 (1993). In addition, SEQ. ID NOS. 1 and 2 herein present the full length sequences of the murine MPL receptor gene and protein, respectively, while SEQ. ID NOS. 3 and 4 present the full length sequences of the murine MPL receptor gene and protein, respectively.

In the murine sequence (SEQ. ID NO. 2), the domains are as follows:

| | |
|---|---|
| signal peptide | aa 1 (Met) through aa 18 (Ser) |
| extracellular | aa 19 (Gln) through aa 483 (Trp) |
| transmembrane | aa 484 (Ile) through aa 505 (Leu) |
| cytoplasmic | aa 506 (Lys) through aa 626 (Pro) |

Referring again to the murine sequence (SEQ. ID NO. 2), some preferred soluble sequences are:

aa 19 (±10 aa) through aa 483 (±10 aa), and aa 19 (±10 aa) through aa 484 (±10 aa) fused to aa 506 (±10 aa) through aa 626 (±10 aa).

It is known that the human sequence has at least two forms, MPL-P and MPL-K. The P form has the amino acid and gene sequences shown in SEQ. ID NOS. 3 and 4, respectively. In the human MPL-P sequence, the domains are as follows:

| | |
|---|---|
| signal peptide | aa 1 (Met) through aa 25 (Ser) |
| extracellular | aa 26 (Gln) through aa 491 (Trp) |
| transmembrane | aa 492 (Ile) through aa 513 (Leu) |
| cytoplasmic | aa 514 (Arg) through aa 635 (Pro) |

Referring to the human sequence (SEQ. ID NO. 4), some preferred soluble sequences are:

aa 19 (±10 aa) through aa 483 (±10 aa), and aa 19 (±10 aa) through aa 484 (±10 aa) fused to aa 506 (±10 aa) through aa 626 (±10 aa).

Figure 2:
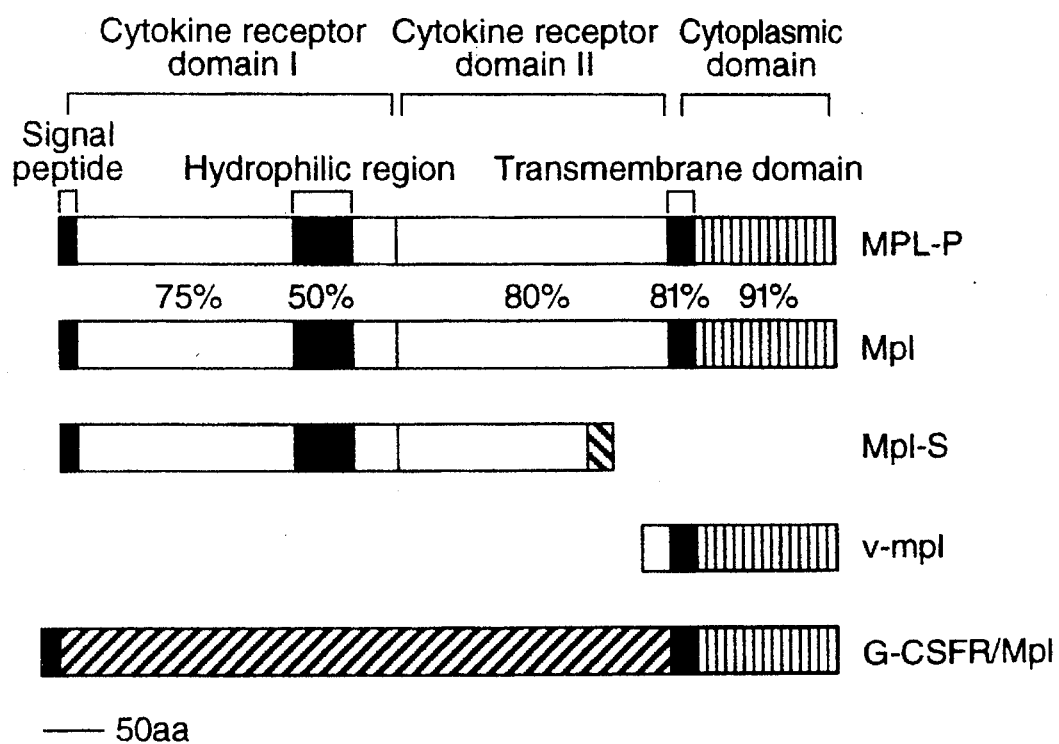
FIG. 2 shows a schematic comparison of the domains of MPL-P (human) and Mpl (murine). Additionally, a schematic depiction of an exemplary soluble form of the receptor is shown (Mpl-S).

With reference to FIG. 2, one example of a soluble form of the receptor is depicted (Mpl-S). It might be possible to remove even a larger portion of cytokine receptor domain II (CRD II) from either of the human or murine sequences and still have a soluble form of the receptor with platelet enhancing activity. Thus, the present inventors also contemplate the use of soluble receptors wherein substantially all of the CRD II domain is removed from the MPL receptor to enhance platelet production in a patient.

As exemplified above, based on the known MPL sequences and the prior publications in this area or routine experimentation, one of ordinary skill will be able to readily obtain a family of unbound murine or human MPL receptors for use in the context of this invention.

Various biologically active analogs of the foregoing proteins could also be employed in the methods and compositions of the present invention. As used herein, therefore, the term "MPL receptor" includes proteins having substantial amino acid sequence identity to native mammalian MPL receptor and qualitatively equivalent biological activity, for example, in standard bioassays (e.g., assays of the receptor binding affinity or antibody binding affinity of the analog protein). Particularly preferably, the analogs of the unbound MPL receptor of the present invention are based on the soluble form of the protein. The MPL receptor may further be in pegylated form or fused to other cytokine proteins or fragments thereof, e.g., IL-3, IL-6, IL-11, GM-CSF, EPO, and the like.

Preferred methods for producing mammalian MPL receptors Of the present invention involve recombinant expression in mammalian cells, although such proteins can also be produced recombinantly using insect cells, yeast, bacteria, or other cells under the control of appropriate promoters. Appropriate cloning and expression vectors for use with bacterial, fungal, yeast, and mammalian cellular hosts are described by Powels et al., *Cloning Vectors: A Laboratory Manual*(Elsevier New York, 1985). Various mammalian cell culture systems can be employed to express recombinant protein.

Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, 293, HeLa and BHK cell lines. Mammalian expression vectors may comprise nontranscribed elements such as an origin of replication, a suitable promoter and enhancer, and other 5' or 3' flanking nontranscribed sequences, and 5' or 3' nontranslated sequences, such as necessary ribosome binding sites; a polyadenylation site; splice donor and acceptor sequences; and termination sequences. DNA sequences derived from the SV40 viral genome, for example, SV40 origin, early promoter, enhancer, splice, and polyadenylation sites, may be used to provide the other genetic elements required for expression of a heterologous DNA sequence. Additional details regarding the use of mammalian high expression vectors to produce a recombinant mammalian MPL receptor are provided below. Exemplary vectors can be constructed as disclosed by Okayarea and Berg, *Mol. Cell. Biol.* 3:280 (1983); Cosman et al., *Nature* 312:768 (1984); Cosman et al., *Mol. Immunol.* 23:935 (1986); and Clark et al., U.S. Pat. No. 4,675,285.

The conditions to be treated by the methods and compositions of the present invention are generally those which involve an existing platelet deficiency or an expected platelet deficiency in the future (e.g., because of planned surgery). The generic term for platelet deficiency is thrombocytopenia, and hence the methods and compositions of the present invention are generally available for treating thrombocytopenias.

Thrombocytopenias (platelet deficiencies) may be present for various reasons, including chemotherapy, radiation therapy, surgery, accidental blood loss, and other specific disease conditions. Exemplary specific disease conditions that involve thrombocytopenia and may be treated in accordance with this invention are: aplastic anemia, idiopathic thrombocytopenia, and certain metastatic tumors which result in thrombocytopenia. Also, certain treatments for AIDS result in thrombocytopenia (e.g., AZT). Certain wound healing disorders might also benefit from an increase in platelet numbers.

With regard to anticipated platelet deficiencies, e.g., due to future surgery, the MPL receptor could be administered several days to several hours prior to the need for platelets. With regard to acute situations, e.g., accidental and massive blood loss, the MPL receptor could be administered along with blood or purified platelets.

The specific dosage amount of unbound MPL receptor to be administered in connection with these conditions will be affected by a number of variables, including: the weight, sex, age, and general condition of the patient to be treated; the nature of the condition to be treated; the mode of administration; the urgency of the situation; and others. In acute situations, the dose to be administered will generally be larger than with chronic conditions or conditions with lesser platelet deficiency.

The compositions of the present invention include a "pharmaceutically acceptable carrier" in which the unbound receptor is soluble. The carrier material may be water for injection, preferably supplemented with other materials common in solutions for administration to mammals. Typically, an MPL receptor therapeutic will be administered in the form of a composition comprising purified protein in conjunction with physiologically acceptable carriers, excipients, or diluents. Neutral buffered saline or saline mixed with serum albumin are exemplary appropriate diluents. Preferably, the product is formulated as a lyophilizate using appropriate excipient solutions (e.g., sucrose) as diluents. Other standard carriers, diluents, and excipients may be included as desired.

EXAMPLES

The following examples are included to more fully illustrate the present invention. Additionally, these examples provide preferred embodiments of the invention, but are not meant to limit the scope thereof, unless so indicated. Standard methods for many of the procedures described in the following examples, or suitable alternative procedures, are provided in widely recognized manuals of molecular biology such as, for example, Sambrook et al., "Molecular Cloning," Second Edition, Cold Spring Harbor Laboratory Press (1987) and in Ausubel et al., (Eds), "Current Protocols in Molecular Biology," Greene Associates/Wiley Interscience, New York (1990).

EXAMPLE 1

Isolation Of Nucleic Acid Sequences Encoding An MPL Receptor

The isolation of clones encoding the murine (Vigon et al. *Oncogene* 8:2607–2615 (1993) and (Skoda et al., *EMBO*) 12

(7):2645–2653 (1993)) and human (Vigon et al., *DNAS* 89:5640–5644 (1992)) isoforms of the MPL receptor have been reported. The DNA sequence of these are available from the GenBank database as accession numbers X73677 and Z22657 for the murine receptor and M90102 and M90103 for the K and P isoforms of the human receptor. It has further been reported that spleen, bone marrow, placenta and fetal liver are all tissues which express mRNA for MPL. Cell lines which express MPL include HEL. It thus becomes clear to one skilled in the art, how to isolate clones encoding MPL. cDNA could be generated from one of the above tissue sources or cell line, or from another source identified to express MPL by Northern blot analysis of RNA or Western blot analysis of protein.

This cDNA serves as a source of material for the generation of a cDNA library in an appropriate vector. This library is screened by hybridization to a nucleic acid probe to identify cells containing the MPL gene. Alternatively the cDNA library is screened for expression of MPL using an antibody. This antibody is generated against a synthetic oligo-peptide corresponding to the MPL sequence.

The cDNA can also serve as a template for PCR amplification of the MPL gene. The primers are chosen from sequences in the MPL gene and may incorporate additional sequences to aid in the cloning and expression of MPL.

EXAMPLE 2

Isolation Of Clones For Expression Of Soluble Murine MPL

Using a clone containing MPL as identified above, or cDNA from a source capable of expressing MPL, the PCR technique is used to obtain a clone for expression of soluble MPL. Primers for PCR amplification of murine MPL may be of the form:

5' primer:
   TAC AAG CTT GCC GTC ATC ATG CCC TCT TGG GCC CTC (SEQ. ID NO. 5); and
3' primer:
   ACT TCT AGA CTA TCA AGC AGT CTC GGA GCT GGA (SEQ. ID NO. 6)

PCR reactions are carried out using 1 µl of a cDNA reaction mix, 5 pmol of each of the above oligonucleotides, 10 mM Tris HCl (pH 8.3), 50 mM KCl, 1.5 mM Mg Cl$_2$, 200 µM each dNTP and 1 unit of Taq polymerase. Amplification is for 35 cycles of 30 sec. at 94° C., 30 sec. at 50° C., 1 min at 72° C. DNA is then purified by agarose gel electrophoresis, digested with Hind III and XbaI and ligated into the expression vector pDSRα2 digested with Hind III and XbaI. Clones containing the desired insert are verified by DNA sequence analysis.

EXAMPLE 3

Expression Of Soluble Murine MPL In CHO Cells

The expression plasmid pDSR2-MPL-X contains sequences encoding murine MPL amino acids as shown in (SEQ. ID NOS. 7 and 8). Ten micrograms of this plasmid were introduced into CHO cells by calcium phosphate mediated transfection (Wigler et al., *Cell* 11:233 (1977)). Individual colonies were selected based upon expression of the dihydrofolate reductase gene from the vector. Expression of soluble MPL was monitored by RNA hybridization (Hunt et al., *Exp. Hematol,* 19:779 (1991)) and by Western blotting using an antibody generated to a synthetic peptide corresponding to amino acids 459 (Gly) to 475 (Val) of SEQ. ID NO. 2. *Cell* line B.1–18 was positive in these assays and was selected for further expansion. The cell line was adapted to 30 nM Methotrexate (Mtx) to stimulate amplification of MPL expression. Roller bottles were inoculated with 2×10$^7$ cells in 200 ml DMEM: Ham's F12 (1:1) supplemented with non-essential amino acids (NEAA), 30 nM Mtx and 5% fetal bovine serum (FBS) (reagents from GIBCO, Grand Island, N.Y.). Upon reaching confluence in 3–4 days, the media was replaced with 200 ml DMEM: Ham's F12, NEAA, 30 nM Mtx with no serum. Conditioned media was harvested after 6–7 days and replaced with fresh serum-free media. Second and third harvests were collected.

EXAMPLE 4

Purification Of Soluble Murine MPL

The recombinant, extracellular domain of the murine MPL gene product (m-MPL-X) was purified from CHO cell conditioned media by sequential ion exchange and hydroxyapatite chromatography. Conditioned media containing m-MPL-X was concentrated 10× by ultrafiltration with a 30,000 MW cutoff membrane (S10Y30, Amicon, Danvers, Mass.) and diafiltered against 10 mM Tris-HCL, pH 8.5. The concentrate was loaded onto a column of Q-Sepharose, fast flow (Pharmacia, Piscataway, N.J.), washed with 10 mM Tris-HCL, pH 8.5, and eluted with a linear gradient of 0M–1.0M NaCl in the same buffer. Fractions from the column were analyzed for m-MPL-X by SDS-PAGE and Western blotting, using an antiserum generated against purified m-MPL-X. Fractions containing m-MPL-X were pooled, diafiltered against 10 mM sodium phosphate, 0.01 mM CaCl$_2$, pH 6.8, and applied to a hydroxyapatite column (HA-Ultragel, Sepracor, Malborough, Mass.). The unbound fraction, containing purified m-MPL-X was diluted into PBS, sterile filtered, and aseptically dispensed in appropriate volumes at a final concentration of 0.10 mg/ml. The purified m-MPL-X was stored frozen at −80° C. until use.

The Limulus Amebocyte Lysate assay (Associates of Cape Cod, Inc., Woods Hole, Mass.) was performed, and the final product was shown to be free of pyrogen 0.004 EU/mg). Analysis of 20 µg of purified m-MPL-X by SDS-PAGE with Coomassie staining demonstrated the presence of a single band with apparent molecular weight of 64 KD. No other protein bands were detected.

EXAMPLE 5

The Effect Of MPL-X On Proplatelet Formation

Guinea pig megakaryocytes were purified and cultured at 5000 cells per well (96-well microtiter plate) with or without MPL-X (30 µg/ml; prepared as described above) for 18 hours. The basal media was Iscove's media supplemented either with BSA (100 µg/ml) or with 10% normal human heparinized plasma (pooled from AB donors). After culture, cells were examined microscopically and scored for proplatelet formations as described by Hunt et al. See Hunt, P. et al., *Exp. Hematol.* 21:372–281 (1993) and Hunt, P. et al., *Exp. Hematol.* 21:1295–1304 (1993). Data is presented as the mean of duplicate determinations±standard error of the mean (SEM).

Figure 3:
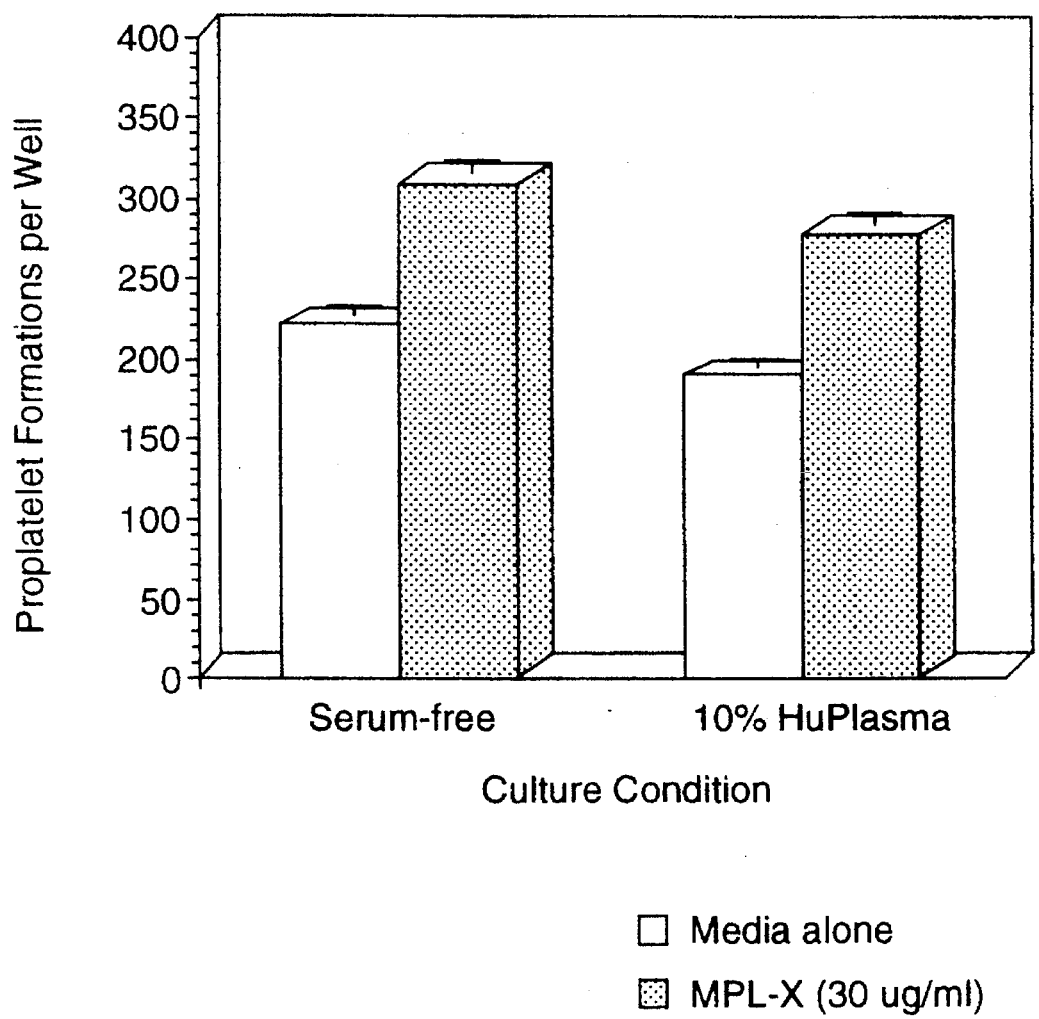
FIG. 3 shows data demonstrating that the addition of soluble MPL receptor (MPL-X) to megakaryocyte cultures enhances the development of proplatelet formations.

Guinea pig megakaryocytes cultured in serum-free media or in heparinized plasma have previously been shown to develop proplatelet formations after 18 hours of culture. See Hunt, P. et al., *Exp. Hematol.* 21:372–281 (1993) and Hunt, P. et al., *Exp. Hematol.* 21:1295–1304 (1993). As shown in FIG. 3, the addition of MPL-X to megakaryocyte cultures resulted in a significant increase in the number of cells developing proplatelet formations. This was observed whether the cells were cultured under serum-free conditions or in the presence of heparinized plasma.

EXAMPLE 6

The Effect Of MPL-X On In Vivo Proplatelet Formation

MPL-X was diluted to 100 μg/ml or 10 μg/ml into carrier (PBS+0.2% normal Balb/c mouse sera). In addition, 100 μg/ml of bovine serum albumin (BSA) or heat-inactivated MPL-X (98° C.; 15 minutes) were used. Balb/c mice (female, 6–8 weeks of age, Charles River) were injected subcutaneously twice daily, with an 8 hour interval, with 0.5 ml of each test solution for up to 42 days. On the indicated days, animals were bled from the lateral tail vein through a small incision made with a scalpel blade. Twenty microliters of blood were collected and diluted immediately into manufacturer's diluent for the Sysmex cell analyzer (TOA Medical Electronics, Kobe, Japan). White blood cell (WBC), red blood cell (RBC), and platelet counts were obtained. Data are expressed as the mean of the indicated number of samples±SEM.

Figure 5:
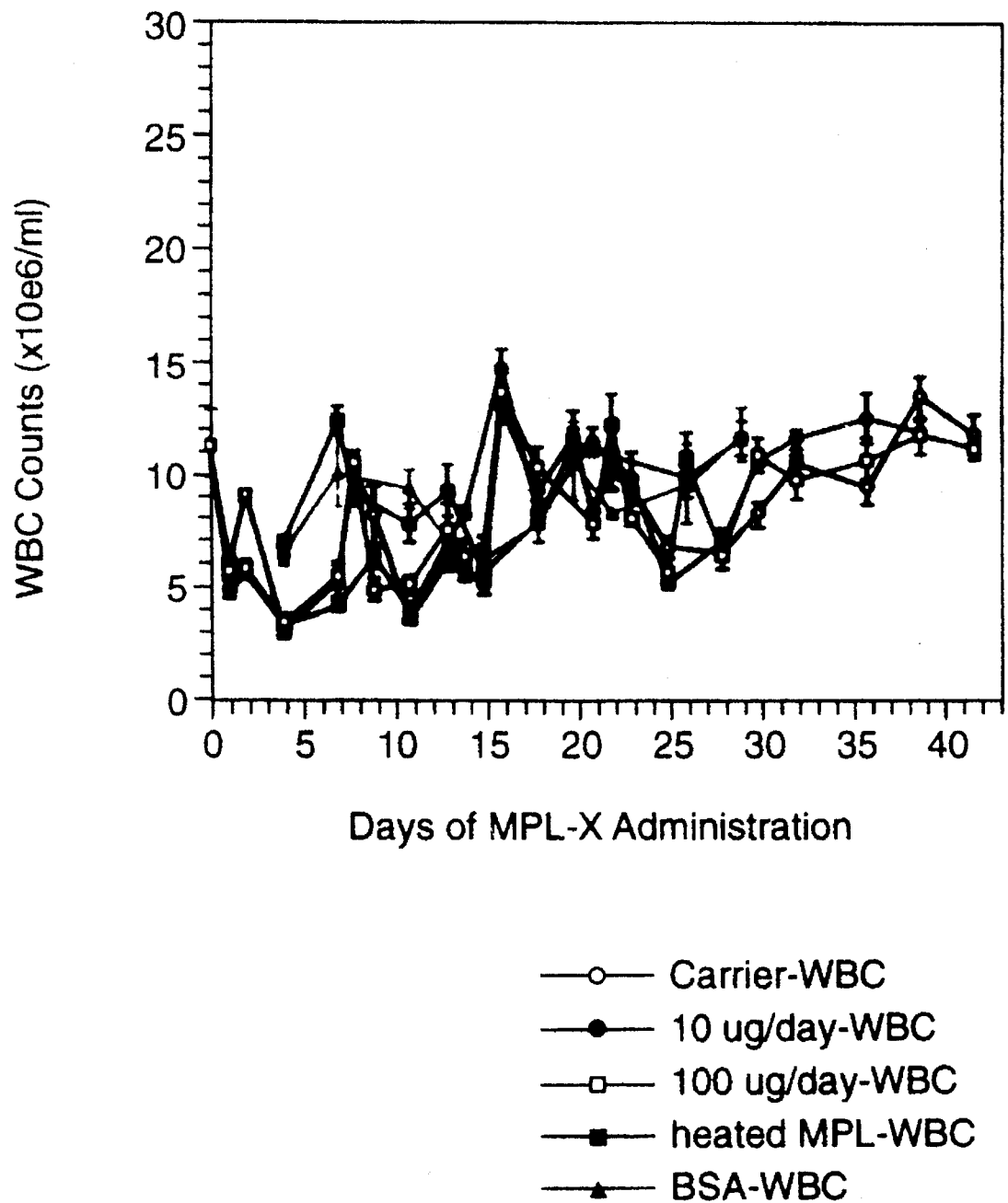
FIG. 5 presents data showing the effect of MPL-X in vivo on white blood cell (WBC) counts in a mouse model.
Figure 6:
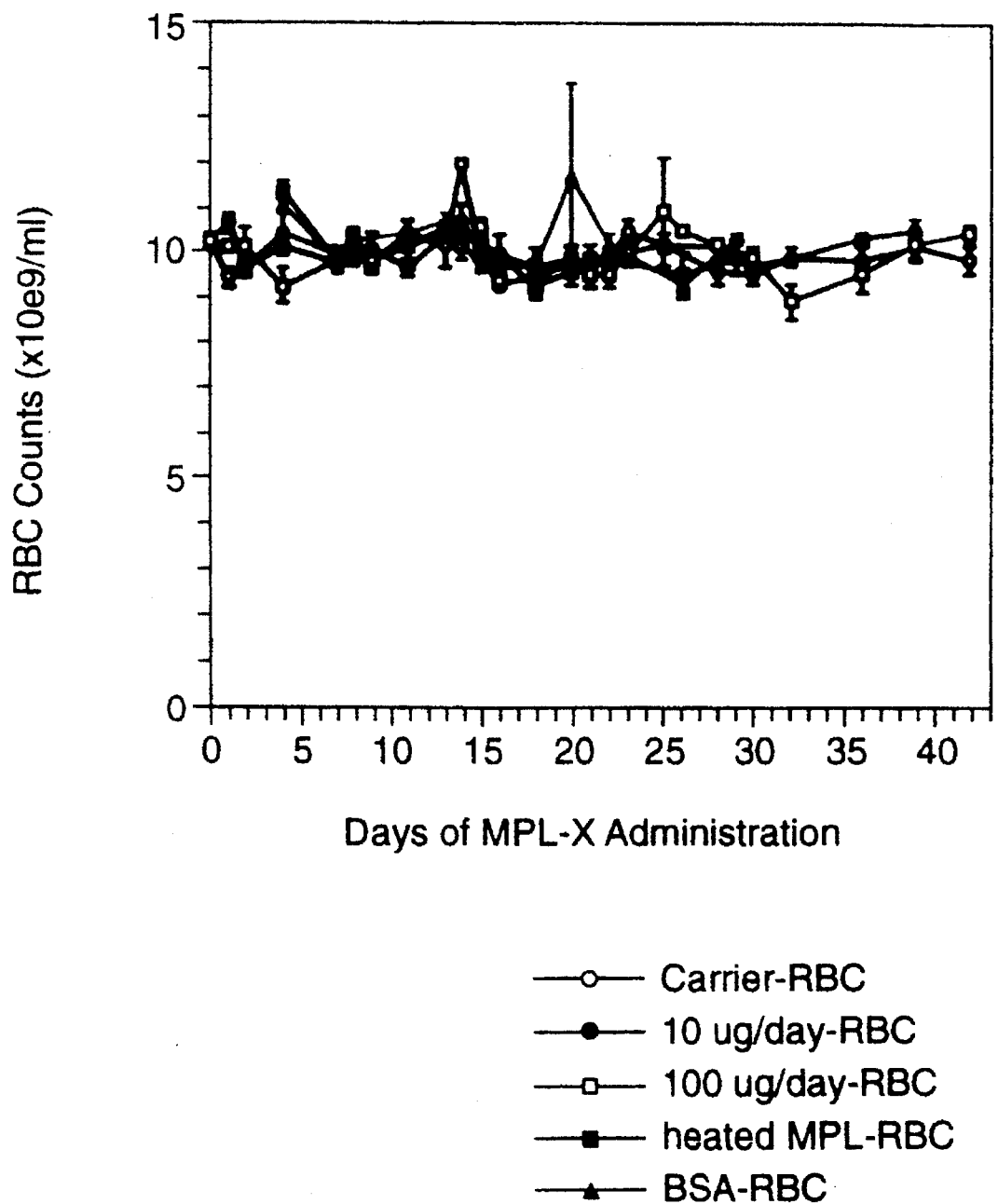
FIG. 6 presents data showing the effect of MPL-X in vivo on red blood cell (RBC) counts in a mouse model.

In order to determine directly the effect of MPL-X on platelet levels, the protein was injected twice daily into normal Balb/c mice. The data from two separate experiments were combined for presentation. In Experiment 1, five mice per group were injected either with carrier, 10 μg/day MPL-X, or 100 μg/day MPL-X for 42 days. In Experiment 2, four mice per group were injected either with carrier, 100 μg/day MPL-X, 100 μg/day heat-inactivated MPL-X or 100 μg/day BSA for 29 days. Whenever data from both experiments were collected from the same time point, they were combined for analysis (N=9, days 0, 4, 7, 11, 18; N=4 or 5, all other days). As shown in FIG. 4, injection of 100 μg/day MPL-X resulted in a significant increase in platelet counts. The effect was first observed after 4–7 days of treatment where platelet levels reached 132% normal levels. Although by Day 11 platelet counts had returned to normal, with continued administration of MPL-X, they again rose reaching 219% of normal by Day 18. After 20 days of treatment, the platelet counts had dropped to 150% of normal. When the study was terminated at 42 days, platelet counts were still 130% of normal. As also shown in FIG. 4, administration of 10 μg/day of MPL-X, 100 μg/day of BSA or heat inactivated MPL-X had no effect on platelet counts. MPL-X administration had no effect on other blood cell parameters. FIGS. 5 and 6 illustrate the data on white blood cell counts and red blood cell counts.

These data indicate that the administration of MPL-x in vivo results in a significant increase in circulating platelets. The response appears to be cyclic with a periodicity of approximately 7–10 days. No other blood cell parameter was affected at any time point measured.

While the present invention has been described above both generally and in terms of preferred embodiments, it is understood that variations and modifications will occur to those skilled in the art in light of the above description. Therefore, it is intended that the appended claims cover all such variations coming within the scope of the invention as claimed.

Additionally, the publications and other materials cited to illuminate the background of the invention, and in particular cases to provide additional details concerning its practice, are herein incorporated by reference.

What is claimed is:

1. A method for increasing the number of platelets in a mammal, which comprises administering to the mammal a platelet number increasing effective amount of a soluble MPL receptor, wherein said soluble MPL receptor has an amino acid sequence of SEQ ID NO: 2 that begins at an amino acid residue of from 9 to 29 and ends at an amino acid residue of from 473 to 493.

2. A method for increasing the number of platelets in a mammal, which comprises administering to the mammal a platelet number increasing effective amount of a soluble MPL receptor, wherein said soluble MPL receptor has an amino acid sequence of SEQ ID NO: 4 that begins at an amino acid residue of from 16 to 36 and ends at an amino acid residue of from 481 to 501.

3. A method according to claim 1 or 2, wherein said mammal is human.

4. A method according to claim 1 or 2, wherein said mammal is suffering from a platelet deficiency.

5. A method according to claim 1 or 2, wherein the soluble MPL receptor is administered intravenously.

6. A method according to claim 1 or 2, wherein said platelet number increasing effective amount is from about 1 mg per kg to about 100 mg per kg per day.

* * * * *

UNITED STATES PATENT AND TRADEMARK OFFICE
CERTIFICATE OF CORRECTION

PATENT NO. : 5,498,599
DATED : March 12, 1996
INVENTOR(S) : Esther S. Choi, Martha M. Hokom, Pamela Hunt, Janet L. Nichol It is certified that error appears in the above-identified patent and that said Letters Patent is hereby corrected as shown below:

Column 8, line 41, "murine" should be --human--.

Column 9, line 62, "Okayarea" should be --Okayama--.

Column 11, line 58, "pDSR2-MPL-X" should be -- pDSR$\alpha$2 -MPL-X --.

Column 12, line 43, "0.004" should be --<0.004--.

Column 13, line 3, "FIG. 3" should be --FIG. 4--.

Signed and Sealed this

Third Day of December, 1996

BRUCE LEHMAN

*Attest:*

*Attesting Officer*     *Commissioner of Patents and Trademarks*

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 2046 base pairs
        ( B ) TYPE: nucleic acid
        ( C ) STRANDEDNESS: unknown
        ( D ) TOPOLOGY: unknown ( i i ) MOLECULE TYPE: cDNA ( i x ) FEATURE:
        ( A ) NAME/KEY: CDS
        ( B ) LOCATION: 8..1888

( x i ) SEQUENCE DESCRIPTION: SEQ ID NO:1:

```
CCTCTTC ATG GTC ACC TCC TGC CTC CTC TTG GCC CTT CCA AAC CAG GCA        49
        Met Val Thr Ser Cys Leu Leu Leu Ala Leu Pro Asn Gln Ala
        1               5                   10

CAA GTC ACC AGC CAA GAT GTC TTC TTG CTG GCC TTG GGC ACA GAG CCC        97
Gln Val Thr Ser Gln Asp Val Phe Leu Leu Ala Leu Gly Thr Glu Pro
15              20                  25                  30

CTG AAC TGC TTC TCC CAA ACA TTT GAG GAC CTC ACC TGC TTC TGG GAT        145
Leu Asn Cys Phe Ser Gln Thr Phe Glu Asp Leu Thr Cys Phe Trp Asp
                35                  40                  45
```

| | | | | | | | | | | | | | | | | |
|---|---|---|---|---|---|---|---|---|---|---|---|---|---|---|---|---|
| GAG | GAA | GAG | GCA | GCA | CCC | AGT | GGG | ACA | TAC | CAG | CTG | CTG | TAT | GCC | TAC | 193 |
| Glu | Glu | Glu | Ala | Ala | Pro | Ser | Gly | Thr | Tyr | Gln | Leu | Leu | Tyr | Ala | Tyr | |
| | | | 50 | | | | | 55 | | | | | | 60 | | |
| CGA | GGA | GAG | AAG | CCC | CGT | GCA | TGC | CCC | CTG | TAT | TCC | CAG | AGT | GTG | CCC | 241 |
| Arg | Gly | Glu | Lys | Pro | Arg | Ala | Cys | Pro | Leu | Tyr | Ser | Gln | Ser | Val | Pro | |
| | | | 65 | | | | 70 | | | | | 75 | | | | |
| ACC | TTT | GGA | ACC | CGG | TAT | GTG | TGC | CAG | TTT | CCA | GCC | CAG | GTA | GAA | GTG | 289 |
| Thr | Phe | Gly | Thr | Arg | Tyr | Val | Cys | Gln | Phe | Pro | Ala | Gln | Val | Glu | Val | |
| | | 80 | | | | 85 | | | | | 90 | | | | | |
| CGC | CTC | TTC | TTT | CCG | CTG | CAC | CTC | TGG | GTG | AAG | AAT | GTG | TCC | CTC | AAC | 337 |
| Arg | Leu | Phe | Phe | Pro | Leu | His | Leu | Trp | Val | Lys | Asn | Val | Ser | Leu | Asn | |
| 95 | | | | | 100 | | | | | 105 | | | | | 110 | |
| CAG | ACT | TTG | ATC | CAG | CGG | GTG | CTG | TTT | GTG | GAT | AGT | GTG | GGC | CTG | CCA | 385 |
| Gln | Thr | Leu | Ile | Gln | Arg | Val | Leu | Phe | Val | Asp | Ser | Val | Gly | Leu | Pro | |
| | | | | 115 | | | | | 120 | | | | | 125 | | |
| GCT | CCC | CCC | AGG | GTC | ATC | AAG | GCC | AGG | GGT | GGG | AGC | CAA | CCA | GGG | GAA | 433 |
| Ala | Pro | Pro | Arg | Val | Ile | Lys | Ala | Arg | Gly | Gly | Ser | Gln | Pro | Gly | Glu | |
| | | | 130 | | | | | 135 | | | | | 140 | | | |
| CTT | CAG | ATC | CAC | TGG | GAG | GCC | CCT | GCT | CCT | GAA | ATC | AGT | GAC | TTC | CTG | 481 |
| Leu | Gln | Ile | His | Trp | Glu | Ala | Pro | Ala | Pro | Glu | Ile | Ser | Asp | Phe | Leu | |
| | | 145 | | | | | 150 | | | | | 155 | | | | |
| AGG | CAT | GAA | CTC | CGC | TAT | GGC | CCC | ACG | GAT | TCC | AGC | AAC | GCC | ACT | GCC | 529 |
| Arg | His | Glu | Leu | Arg | Tyr | Gly | Pro | Thr | Asp | Ser | Ser | Asn | Ala | Thr | Ala | |
| | 160 | | | | | 165 | | | | | 170 | | | | | |
| CCC | TCC | GTC | ATT | CAG | CTG | CTC | TCC | ACA | GAA | ACC | TGC | TGC | CCC | ACT | TTG | 577 |
| Pro | Ser | Val | Ile | Gln | Leu | Leu | Ser | Thr | Glu | Thr | Cys | Cys | Pro | Thr | Leu | |
| 175 | | | | | 180 | | | | | 185 | | | | | 190 | |
| TGG | ATG | CCG | AAC | CCA | GTC | CCT | GTT | CTT | GAC | CAG | CCT | CCG | TGT | GTT | CAT | 625 |
| Trp | Met | Pro | Asn | Pro | Val | Pro | Val | Leu | Asp | Gln | Pro | Pro | Cys | Val | His | |
| | | | | 195 | | | | | 200 | | | | | 205 | | |
| CCG | ACA | GCA | TCC | CAA | CCG | CAT | GGA | CCA | GTG | AGG | ACC | TCC | CCA | GCT | GGA | 673 |
| Pro | Thr | Ala | Ser | Gln | Pro | His | Gly | Pro | Val | Arg | Thr | Ser | Pro | Ala | Gly | |
| | | | 210 | | | | | 215 | | | | | 220 | | | |
| GAA | GCT | CCA | TTT | CTG | ACA | GTG | AAG | GGT | GGA | AGC | TGT | CTC | GTC | TCA | GGC | 721 |
| Glu | Ala | Pro | Phe | Leu | Thr | Val | Lys | Gly | Gly | Ser | Cys | Leu | Val | Ser | Gly | |
| | | 225 | | | | | 230 | | | | | 235 | | | | |
| CTC | CAG | GCT | AGC | AAA | TCC | TAC | TGG | CTC | CAG | CTA | CGC | AGC | CAA | CCC | GAC | 769 |
| Leu | Gln | Ala | Ser | Lys | Ser | Tyr | Trp | Leu | Gln | Leu | Arg | Ser | Gln | Pro | Asp | |
| | | 240 | | | | | 245 | | | | | 250 | | | | |
| GGG | GTC | TCC | CTT | CGT | GGC | TCC | TGG | GGA | CCC | TGG | TCC | TTC | CCT | GTG | ACT | 817 |
| Gly | Val | Ser | Leu | Arg | Gly | Ser | Trp | Gly | Pro | Trp | Ser | Phe | Pro | Val | Thr | |
| 255 | | | | | 260 | | | | | 265 | | | | | 270 | |
| GTG | GAT | CTT | CCA | GGA | GAT | GCA | GTG | ACA | ATT | GGA | CTT | CAG | TGC | TTT | ACC | 865 |
| Val | Asp | Leu | Pro | Gly | Asp | Ala | Val | Thr | Ile | Gly | Leu | Gln | Cys | Phe | Thr | |
| | | | | 275 | | | | | 280 | | | | | 285 | | |
| TTG | GAT | CTG | AAG | ATG | GTC | ACC | TGC | CAG | TGG | CAG | CAA | CAA | GAC | CGC | ACT | 913 |
| Leu | Asp | Leu | Lys | Met | Val | Thr | Cys | Gln | Trp | Gln | Gln | Gln | Asp | Arg | Thr | |
| | | | 290 | | | | | 295 | | | | | 300 | | | |
| AGC | TCC | CAA | GGC | TTC | TTC | CGT | CAC | AGC | AGG | ACG | AGG | TGC | TGC | CCC | ACA | 961 |
| Ser | Ser | Gln | Gly | Phe | Phe | Arg | His | Ser | Arg | Thr | Arg | Cys | Cys | Pro | Thr | |
| | | 305 | | | | | 310 | | | | | 315 | | | | |
| GAC | AGG | GAC | CCC | ACC | TGG | GAG | AAA | TGT | GAA | GAG | GAG | GAA | CCG | CGT | CCA | 1009 |
| Asp | Arg | Asp | Pro | Thr | Trp | Glu | Lys | Cys | Glu | Glu | Glu | Glu | Pro | Arg | Pro | |
| | 320 | | | | | 325 | | | | | 330 | | | | | |
| GGA | TCA | CAG | CCC | GCT | CTC | GTC | TCC | CGC | TGC | CAC | TTC | AAG | TCA | CGA | AAT | 1057 |
| Gly | Ser | Gln | Pro | Ala | Leu | Val | Ser | Arg | Cys | His | Phe | Lys | Ser | Arg | Asn | |
| 335 | | | | | 340 | | | | | 345 | | | | | 350 | |
| GAC | AGT | GTT | ATT | CAC | ATC | CTT | GTA | GAG | GTG | ACC | ACA | GCG | CAA | GGT | GCC | 1105 |
| Asp | Ser | Val | Ile | His | Ile | Leu | Val | Glu | Val | Thr | Thr | Ala | Gln | Gly | Ala | |
| | | | | 355 | | | | | 360 | | | | | 365 | | |

| | | | | | | | | | | | | | | | | |
|---|---|---|---|---|---|---|---|---|---|---|---|---|---|---|---|---|
| GTT | CAC | AGC | TAC | CTG | GGC | TCC | CCT | TTT | TGG | ATC | CAC | CAG | GCT | GTG | CTC | 1153 |
| Val | His | Ser | Tyr | Leu | Gly | Ser | Pro | Phe | Trp | Ile | His | Gln | Ala | Val | Leu | |
| | | | 370 | | | | | 375 | | | | | 380 | | | |
| CTT | CCC | ACC | CCG | AGC | CTG | CAC | TGG | AGG | GAG | GTC | TCA | AGT | GGA | AGG | CTG | 1201 |
| Leu | Pro | Thr | Pro | Ser | Leu | His | Trp | Arg | Glu | Val | Ser | Ser | Gly | Arg | Leu | |
| | | | 385 | | | | | 390 | | | | | 395 | | | |
| GAG | TTG | GAG | TGG | CAG | CAC | CAG | TCA | TCT | TGG | GCA | GCT | CAA | GAG | ACC | TGC | 1249 |
| Glu | Leu | Glu | Trp | Gln | His | Gln | Ser | Ser | Trp | Ala | Ala | Gln | Glu | Thr | Cys | |
| | | | 400 | | | | | 405 | | | | | 410 | | | |
| TAC | CAG | CTC | CGG | TAC | ACG | GGA | GAA | GGC | CGT | GAG | GAC | TGG | AAG | GTG | CTG | 1297 |
| Tyr | Gln | Leu | Arg | Tyr | Thr | Gly | Glu | Gly | Arg | Glu | Asp | Trp | Lys | Val | Leu | |
| 415 | | | | | 420 | | | | | 425 | | | | | 430 | |
| GAG | CCA | TCT | CTC | GGT | GCC | CGG | GGA | GGG | ACC | CTA | GAG | CTG | CGC | CCC | CGA | 1345 |
| Glu | Pro | Ser | Leu | Gly | Ala | Arg | Gly | Gly | Thr | Leu | Glu | Leu | Arg | Pro | Arg | |
| | | | | 435 | | | | | 440 | | | | | 445 | | |
| GCT | CGC | TAC | AGC | TTG | CAG | CTG | CGT | GCC | AGG | CTC | AAC | GGC | CCC | ACC | TAC | 1393 |
| Ala | Arg | Tyr | Ser | Leu | Gln | Leu | Arg | Ala | Arg | Leu | Asn | Gly | Pro | Thr | Tyr | |
| | | | 450 | | | | | 455 | | | | | 460 | | | |
| CAA | GGT | CCC | TGG | AGC | GCC | TGG | TCT | CCC | CCA | GCT | AGG | GTG | TCC | ACG | GGC | 1441 |
| Gln | Gly | Pro | Trp | Ser | Ala | Trp | Ser | Pro | Pro | Ala | Arg | Val | Ser | Thr | Gly | |
| | | | 465 | | | | | 470 | | | | | 475 | | | |
| TCC | GAG | ACT | GCT | TGG | ATC | ACC | TTG | GTG | ACT | GCT | CTC | CTC | CTG | GTG | CTG | 1489 |
| Ser | Glu | Thr | Ala | Trp | Ile | Thr | Leu | Val | Thr | Ala | Leu | Leu | Leu | Val | Leu | |
| | | | 480 | | | | | 485 | | | | | 490 | | | |
| AGC | CTC | AGT | GCC | CTT | CTG | GGC | CTA | CTG | CTA | AAG | TGG | CAA | TTT | CCT | | 1537 |
| Ser | Leu | Ser | Ala | Leu | Leu | Gly | Leu | Leu | Leu | Lys | Trp | Gln | Phe | Pro | | |
| 495 | | | | | 500 | | | | | 505 | | | | | 510 | |
| GCG | CAC | TAC | AGG | AGA | CTG | AGG | CAT | GCT | TTG | TGG | CCC | TCG | CTT | CCA | GAC | 1585 |
| Ala | His | Tyr | Arg | Arg | Leu | Arg | His | Ala | Leu | Trp | Pro | Ser | Leu | Pro | Asp | |
| | | | | 515 | | | | | 520 | | | | | 525 | | |
| CTA | CAC | CGG | GTC | CTA | GGC | CAG | TAC | CTC | AGA | GAC | ACT | GCA | GCC | CTA | AGT | 1633 |
| Leu | His | Arg | Val | Leu | Gly | Gln | Tyr | Leu | Arg | Asp | Thr | Ala | Ala | Leu | Ser | |
| | | | 530 | | | | | 535 | | | | | 540 | | | |
| CCT | TCT | AAG | GCC | ACG | GTT | ACC | GAT | AGC | TGT | GAA | GAA | GTG | GAA | CCC | AGC | 1681 |
| Pro | Ser | Lys | Ala | Thr | Val | Thr | Asp | Ser | Cys | Glu | Glu | Val | Glu | Pro | Ser | |
| | | 545 | | | | | 550 | | | | | 555 | | | | |
| CTC | CTG | GAA | ATC | CTC | CCT | AAA | TCC | TCA | GAG | AGC | ACT | CCT | TTA | CCT | CTG | 1729 |
| Leu | Leu | Glu | Ile | Leu | Pro | Lys | Ser | Ser | Glu | Ser | Thr | Pro | Leu | Pro | Leu | |
| | 560 | | | | | 565 | | | | | 570 | | | | | |
| TGT | CCC | TCC | CAA | CCT | CAG | ATG | GAC | TAC | AGA | GGA | CTG | CAA | CCT | TGC | CTG | 1777 |
| Cys | Pro | Ser | Gln | Pro | Gln | Met | Asp | Tyr | Arg | Gly | Leu | Gln | Pro | Cys | Leu | |
| 575 | | | | | 580 | | | | | 585 | | | | | 590 | |
| CGG | ACC | ATG | CCC | CTG | TCT | GTG | TGT | CCA | CCC | ATG | GCT | GAG | ACG | GGG | TCC | 1825 |
| Arg | Thr | Met | Pro | Leu | Ser | Val | Cys | Pro | Pro | Met | Ala | Glu | Thr | Gly | Ser | |
| | | | | 595 | | | | | 600 | | | | | 605 | | |
| TGC | TGC | ACC | ACA | CAC | ATT | GCC | AAC | CAC | TCC | TAC | CTA | CCA | CTA | AGC | TAT | 1873 |
| Cys | Cys | Thr | Thr | His | Ile | Ala | Asn | His | Ser | Tyr | Leu | Pro | Leu | Ser | Tyr | |
| | | | 610 | | | | | 615 | | | | | 620 | | | |
| TGG | CAG | CAG | CCC | TGAAGGCAGT | CCCCATGCTA | CTGCAGACCT | ATACATTCCT | | | | | | | | | 1925 |
| Trp | Gln | Gln | Pro | | | | | | | | | | | | | |
| | | 625 | | | | | | | | | | | | | | |

ACACACTACC TTATCCATCC TCAACACCAT CCATTCTGTT GCCACCCAC TCCCCCTCTG   1985

GCTTTATAAC ACTGATCACT CCAAGATGGC TGCTCACAAA TCCAGAGCTC TGTCTCTGCA   2045

G   2046

( 2 ) INFORMATION FOR SEQ ID NO:2:

( i ) SEQUENCE CHARACTERISTICS:
        ( A ) LENGTH: 626 amino acids (B) TYPE: amino acid
(D) TOPOLOGY: linear (ii) MOLECULE TYPE: protein (xi) SEQUENCE DESCRIPTION: SEQ ID NO:2:

```
Met Val Thr Ser Cys Leu Leu Leu Ala Leu Pro Asn Gln Ala Gln Val
 1               5                  10                  15
Thr Ser Gln Asp Val Phe Leu Leu Ala Leu Gly Thr Glu Pro Leu Asn
             20                  25                  30
Cys Phe Ser Gln Thr Phe Glu Asp Leu Thr Cys Phe Trp Asp Glu Glu
             35                  40                  45
Glu Ala Ala Pro Ser Gly Thr Tyr Gln Leu Leu Tyr Ala Tyr Arg Gly
         50                  55                  60
Glu Lys Pro Arg Ala Cys Pro Leu Tyr Ser Gln Ser Val Pro Thr Phe
 65                  70                  75                  80
Gly Thr Arg Tyr Val Cys Gln Phe Pro Ala Gln Val Glu Val Arg Leu
                 85                  90                  95
Phe Phe Pro Leu His Leu Trp Val Lys Asn Val Ser Leu Asn Gln Thr
             100                 105                 110
Leu Ile Gln Arg Val Leu Phe Val Asp Ser Val Gly Leu Pro Ala Pro
             115                 120                 125
Pro Arg Val Ile Lys Ala Arg Gly Gly Ser Gln Pro Gly Glu Leu Gln
     130                 135                 140
Ile His Trp Glu Ala Pro Ala Pro Glu Ile Ser Asp Phe Leu Arg His
145                 150                 155                 160
Glu Leu Arg Tyr Gly Pro Thr Asp Ser Ser Asn Ala Thr Ala Pro Ser
                 165                 170                 175
Val Ile Gln Leu Leu Ser Thr Glu Thr Cys Cys Pro Thr Leu Trp Met
             180                 185                 190
Pro Asn Pro Val Pro Val Leu Asp Gln Pro Pro Cys Val His Pro Thr
             195                 200                 205
Ala Ser Gln Pro His Gly Pro Val Arg Thr Ser Pro Ala Gly Glu Ala
     210                 215                 220
Pro Phe Leu Thr Val Lys Gly Gly Ser Cys Leu Val Ser Gly Leu Gln
225                 230                 235                 240
Ala Ser Lys Ser Tyr Trp Leu Gln Leu Arg Ser Gln Pro Asp Gly Val
                 245                 250                 255
Ser Leu Arg Gly Ser Trp Gly Pro Trp Ser Phe Pro Val Thr Val Asp
             260                 265                 270
Leu Pro Gly Asp Ala Val Thr Ile Gly Leu Gln Cys Phe Thr Leu Asp
     275                 280                 285
Leu Lys Met Val Thr Cys Gln Trp Gln Gln Gln Asp Arg Thr Ser Ser
290                 295                 300
Gln Gly Phe Phe Arg His Ser Arg Thr Arg Cys Cys Pro Thr Asp Arg
305                 310                 315                 320
Asp Pro Thr Trp Glu Lys Cys Glu Glu Glu Pro Arg Pro Gly Ser
                 325                 330                 335
Gln Pro Ala Leu Val Ser Arg Cys His Phe Lys Ser Arg Asn Asp Ser
             340                 345                 350
Val Ile His Ile Leu Val Glu Val Thr Thr Ala Gln Gly Ala Val His
             355                 360                 365
Ser Tyr Leu Gly Ser Pro Phe Trp Ile His Gln Ala Val Leu Leu Pro
     370                 375                 380
Thr Pro Ser Leu His Trp Arg Glu Val Ser Ser Gly Arg Leu Glu Leu
```

| | | | | | | | | | | | | | | | |
|---|---|---|---|---|---|---|---|---|---|---|---|---|---|---|---|
| 385 | | | | | 390 | | | | | 395 | | | | | 400 |
| Glu | Trp | Gln | His | Gln | Ser | Ser | Trp | Ala | Ala | Gln | Glu | Thr | Cys | Tyr | Gln |
| | | | | 405 | | | | | 410 | | | | | 415 | |
| Leu | Arg | Tyr | Thr | Gly | Glu | Gly | Arg | Glu | Asp | Trp | Lys | Val | Leu | Glu | Pro |
| | | | 420 | | | | | 425 | | | | | 430 | | |
| Ser | Leu | Gly | Ala | Arg | Gly | Gly | Thr | Leu | Glu | Leu | Arg | Pro | Arg | Ala | Arg |
| | | 435 | | | | | 440 | | | | | 445 | | | |
| Tyr | Ser | Leu | Gln | Leu | Arg | Ala | Arg | Leu | Asn | Gly | Pro | Thr | Tyr | Gln | Gly |
| | 450 | | | | | 455 | | | | | 460 | | | | |
| Pro | Trp | Ser | Ala | Trp | Ser | Pro | Pro | Ala | Arg | Val | Ser | Thr | Gly | Ser | Glu |
| 465 | | | | | 470 | | | | | 475 | | | | | 480 |
| Thr | Ala | Trp | Ile | Thr | Leu | Val | Thr | Ala | Leu | Leu | Leu | Val | Leu | Ser | Leu |
| | | | | 485 | | | | | 490 | | | | | 495 | |
| Ser | Ala | Leu | Leu | Gly | Leu | Leu | Leu | Leu | Lys | Trp | Gln | Phe | Pro | Ala | His |
| | | | 500 | | | | | 505 | | | | | 510 | | |
| Tyr | Arg | Arg | Leu | Arg | His | Ala | Leu | Trp | Pro | Ser | Leu | Pro | Asp | Leu | His |
| | | 515 | | | | | 520 | | | | | 525 | | | |
| Arg | Val | Leu | Gly | Gln | Tyr | Leu | Arg | Asp | Thr | Ala | Ala | Leu | Ser | Pro | Ser |
| | 530 | | | | | 535 | | | | | 540 | | | | |
| Lys | Ala | Thr | Val | Thr | Asp | Ser | Cys | Glu | Glu | Val | Glu | Pro | Ser | Leu | Leu |
| 545 | | | | | 550 | | | | | 555 | | | | | 560 |
| Glu | Ile | Leu | Pro | Lys | Ser | Ser | Glu | Ser | Thr | Pro | Leu | Pro | Leu | Cys | Pro |
| | | | | 565 | | | | | 570 | | | | | 575 | |
| Ser | Gln | Pro | Gln | Met | Asp | Tyr | Arg | Gly | Leu | Gln | Pro | Cys | Leu | Arg | Thr |
| | | | 580 | | | | | 585 | | | | | 590 | | |
| Met | Pro | Leu | Ser | Val | Cys | Pro | Pro | Met | Ala | Glu | Thr | Gly | Ser | Cys | Cys |
| | | 595 | | | | | 600 | | | | | 605 | | | |
| Thr | Thr | His | Ile | Ala | Asn | His | Ser | Tyr | Leu | Pro | Leu | Ser | Tyr | Trp | Gln |
| | 610 | | | | | 615 | | | | | 620 | | | | |
| Gln | Pro | | | | | | | | | | | | | | |
| 625 | | | | | | | | | | | | | | | |

( 2 ) INFORMATION FOR SEQ ID NO:3:

( i ) SEQUENCE CHARACTERISTICS:
        ( A ) LENGTH: 1907 base pairs
        ( B ) TYPE: nucleic acid
        ( C ) STRANDEDNESS: unknown
        ( D ) TOPOLOGY: unknown ( i i ) MOLECULE TYPE: cDNA ( i x ) FEATURE:
        ( A ) NAME/KEY: CDS
        ( B ) LOCATION: 1..1905

( x i ) SEQUENCE DESCRIPTION: SEQ ID NO:3:

| | | | | | | | | | | | | | | | |
|---|---|---|---|---|---|---|---|---|---|---|---|---|---|---|---|
| ATG | CCC | TCC | TGG | GCC | CTC | TTC | ATG | GTC | ACC | TCC | TGC | CTC | CTC | CTG | GCC | 48
| Met | Pro | Ser | Trp | Ala | Leu | Phe | Met | Val | Thr | Ser | Cys | Leu | Leu | Leu | Ala |
| 1 | | | | 5 | | | | | 10 | | | | | 15 | |
| CCT | CAA | AAC | CTG | GCC | CAA | GTC | AGC | AGC | CAA | GAT | GTC | TCC | TTG | CTG | GCA | 96
| Pro | Gln | Asn | Leu | Ala | Gln | Val | Ser | Ser | Gln | Asp | Val | Ser | Leu | Leu | Ala |
| | | | 20 | | | | | 25 | | | | | 30 | | |
| TCA | GAC | TCA | GAG | CCC | CTG | AAG | TGT | TTC | TCC | CGA | ACA | TTT | GAG | GAC | CTC | 144
| Ser | Asp | Ser | Glu | Pro | Leu | Lys | Cys | Phe | Ser | Arg | Thr | Phe | Glu | Asp | Leu |
| | | 35 | | | | | 40 | | | | | 45 | | | |
| ACT | TGC | TTC | TGG | GAT | GAG | GAA | GAG | GCA | GCG | CCC | AGT | GGG | ACA | TAC | CAG | 192
| Thr | Cys | Phe | Trp | Asp | Glu | Glu | Glu | Ala | Ala | Pro | Ser | Gly | Thr | Tyr | Gln |
| | 50 | | | | | 55 | | | | | 60 | | | | |

| | | | | | | | | | | | | | | | | |
|---|---|---|---|---|---|---|---|---|---|---|---|---|---|---|---|---|
| CTG | CTG | TAT | GCC | TAC | CCG | CGG | GAG | AAG | CCC | CGT | GCT | TGC | CCC | CTG | AGT | 240 |
| Leu | Leu | Tyr | Ala | Tyr | Pro | Arg | Glu | Lys | Pro | Arg | Ala | Cys | Pro | Leu | Ser | |
| 65 | | | | 70 | | | | | 75 | | | | | | 80 | |
| TCC | CAG | AGC | ATG | CCC | CAC | TTT | GGA | ACC | CGA | TAC | GTG | TGC | CAG | TTT | CCA | 288 |
| Ser | Gln | Ser | Met | Pro | His | Phe | Gly | Thr | Arg | Tyr | Val | Cys | Gln | Phe | Pro | |
| | | | | 85 | | | | | 90 | | | | | 95 | | |
| GAC | CAG | GAG | GAA | GTG | CGT | CTC | TTC | TTT | CCG | CTG | CAC | CTC | TGG | GTG | AAG | 336 |
| Asp | Gln | Glu | Glu | Val | Arg | Leu | Phe | Phe | Pro | Leu | His | Leu | Trp | Val | Lys | |
| | | | 100 | | | | | 105 | | | | | 110 | | | |
| AAT | GTG | TTC | CTA | AAC | CAG | ACT | CGG | ACT | CAG | CGA | GTC | CTC | TTT | GTG | GAC | 384 |
| Asn | Val | Phe | Leu | Asn | Gln | Thr | Arg | Thr | Gln | Arg | Val | Leu | Phe | Val | Asp | |
| | | 115 | | | | | 120 | | | | | 125 | | | | |
| AGT | GTA | GGC | CTG | CCG | GCT | CCC | CCC | AGT | ATC | ATC | AAG | GCC | ATG | GGT | GGG | 432 |
| Ser | Val | Gly | Leu | Pro | Ala | Pro | Pro | Ser | Ile | Ile | Lys | Ala | Met | Gly | Gly | |
| | 130 | | | | | 135 | | | | | 140 | | | | | |
| AGC | CAG | CCA | GGG | GAA | CTT | CAG | ATC | AGC | TGG | GAG | GAG | CCA | GCT | CCA | GAA | 480 |
| Ser | Gln | Pro | Gly | Glu | Leu | Gln | Ile | Ser | Trp | Glu | Glu | Pro | Ala | Pro | Glu | |
| 145 | | | | | 150 | | | | | 155 | | | | | 160 | |
| ATC | AGT | GAT | TTC | CTG | AGG | TAC | GAA | CTC | CGC | TAT | GGC | CCC | AGA | GAT | CCC | 528 |
| Ile | Ser | Asp | Phe | Leu | Arg | Tyr | Glu | Leu | Arg | Tyr | Gly | Pro | Arg | Asp | Pro | |
| | | | | 165 | | | | | 170 | | | | | 175 | | |
| AAG | AAC | TCC | ACT | GGT | CCC | ACG | GTC | ATA | CAG | CTG | ATT | GCC | ACA | GAA | ACC | 576 |
| Lys | Asn | Ser | Thr | Gly | Pro | Thr | Val | Ile | Gln | Leu | Ile | Ala | Thr | Glu | Thr | |
| | | | 180 | | | | | 185 | | | | | 190 | | | |
| TGC | TGC | CCT | GCT | CTG | CAG | AGG | CCT | CAC | TCA | GCC | TCT | GCT | CTG | GAC | CAG | 624 |
| Cys | Cys | Pro | Ala | Leu | Gln | Arg | Pro | His | Ser | Ala | Ser | Ala | Leu | Asp | Gln | |
| | | 195 | | | | | 200 | | | | | 205 | | | | |
| TCT | CCA | TGT | GCT | CAG | CCC | ACA | ATG | CCC | TGG | CAA | GAT | GGA | CCA | AAG | CAG | 672 |
| Ser | Pro | Cys | Ala | Gln | Pro | Thr | Met | Pro | Trp | Gln | Asp | Gly | Pro | Lys | Gln | |
| | 210 | | | | | 215 | | | | | 220 | | | | | |
| ACC | TCC | CCA | AGT | AGA | GAA | GCT | TCA | GCT | CTG | ACA | GCA | GAG | GGT | GGA | AGC | 720 |
| Thr | Ser | Pro | Ser | Arg | Glu | Ala | Ser | Ala | Leu | Thr | Ala | Glu | Gly | Gly | Ser | |
| 225 | | | | | 230 | | | | | 235 | | | | | 240 | |
| TGC | CTC | ATC | TCA | GGA | CTC | CAG | CCT | GGC | AAC | TCC | TAC | TGG | CTG | CAG | CTG | 768 |
| Cys | Leu | Ile | Ser | Gly | Leu | Gln | Pro | Gly | Asn | Ser | Tyr | Trp | Leu | Gln | Leu | |
| | | | | 245 | | | | | 250 | | | | | 255 | | |
| CGC | AGC | GAA | CCT | GAT | GGG | ATC | TCC | CTC | GGT | GGC | TCC | TGG | GGA | TCC | TGG | 816 |
| Arg | Ser | Glu | Pro | Asp | Gly | Ile | Ser | Leu | Gly | Gly | Ser | Trp | Gly | Ser | Trp | |
| | | | 260 | | | | | 265 | | | | | 270 | | | |
| TCC | CTC | CCT | GTG | ACT | GTG | GAC | CTG | CCT | GGA | GAT | GCA | GTG | GCA | CTT | GGA | 864 |
| Ser | Leu | Pro | Val | Thr | Val | Asp | Leu | Pro | Gly | Asp | Ala | Val | Ala | Leu | Gly | |
| | | 275 | | | | | 280 | | | | | 285 | | | | |
| CTG | CAA | TGC | TTT | ACC | TTG | GAC | CTG | AAG | AAT | GTT | ACC | TGT | CAA | TGG | CAG | 912 |
| Leu | Gln | Cys | Phe | Thr | Leu | Asp | Leu | Lys | Asn | Val | Thr | Cys | Gln | Trp | Gln | |
| | 290 | | | | | 295 | | | | | 300 | | | | | |
| CAA | CAG | GAC | CAT | GCT | AGC | TCC | CAA | GGC | TTC | TTC | TAC | CAC | AGC | AGG | GCA | 960 |
| Gln | Gln | Asp | His | Ala | Ser | Ser | Gln | Gly | Phe | Phe | Tyr | His | Ser | Arg | Ala | |
| 305 | | | | | 310 | | | | | 315 | | | | | 320 | |
| CGG | TGC | TGC | CCC | AGA | GAC | AGG | TAC | CCC | ATC | TGG | GAG | AAC | TGC | GAA | GAG | 1008 |
| Arg | Cys | Cys | Pro | Arg | Asp | Arg | Tyr | Pro | Ile | Trp | Glu | Asn | Cys | Glu | Glu | |
| | | | | 325 | | | | | 330 | | | | | 335 | | |
| GAA | GAG | AAA | ACA | AAT | CCA | GGA | CTA | CAG | ACC | CCA | CAG | TTC | TCT | CGC | TGC | 1056 |
| Glu | Glu | Lys | Thr | Asn | Pro | Gly | Leu | Gln | Thr | Pro | Gln | Phe | Ser | Arg | Cys | |
| | | | 340 | | | | | 345 | | | | | 350 | | | |
| CAC | TTC | AAG | TCA | CGA | AAT | GAC | AGC | ATT | ATT | CAC | ATC | CTT | GTG | GAG | GTG | 1104 |
| His | Phe | Lys | Ser | Arg | Asn | Asp | Ser | Ile | Ile | His | Ile | Leu | Val | Glu | Val | |
| | | 355 | | | | | 360 | | | | | 365 | | | | |
| ACC | ACA | GCC | CCG | GGT | ACT | GTT | CAC | AGC | TAC | CTG | GGC | TCC | CCT | TTC | TGG | 1152 |
| Thr | Thr | Ala | Pro | Gly | Thr | Val | His | Ser | Tyr | Leu | Gly | Ser | Pro | Phe | Trp | |
| | 370 | | | | | 375 | | | | | 380 | | | | | |

| | | | | | | | | | | | | | | | | |
|---|---|---|---|---|---|---|---|---|---|---|---|---|---|---|---|---|
| ATC | CAC | CAG | GCT | GTG | CGC | CTC | CCC | ACC | CCA | AAC | TTG | CAC | TGG | AGG | GAG | 1200 |
| Ile | His | Gln | Ala | Val | Arg | Leu | Pro | Thr | Pro | Asn | Leu | His | Trp | Arg | Glu | |
| 385 | | | | 390 | | | | | 395 | | | | | | 400 | |
| ATC | TCC | AGT | GGG | CAT | CTG | GAA | TTG | GAG | TGG | CAG | CAC | CCA | TCG | TCC | TGG | 1248 |
| Ile | Ser | Ser | Gly | His | Leu | Glu | Leu | Glu | Trp | Gln | His | Pro | Ser | Ser | Trp | |
| | | | | 405 | | | | | 410 | | | | | 415 | | |
| GCA | GCC | CAA | GAG | ACC | TGT | TAT | CAA | CTC | CGA | TAC | ACA | GGA | GAA | GGC | CAT | 1296 |
| Ala | Ala | Gln | Glu | Thr | Cys | Tyr | Gln | Leu | Arg | Tyr | Thr | Gly | Glu | Gly | His | |
| | | | 420 | | | | | 425 | | | | | 430 | | | |
| CAG | GAC | TGG | AAG | GTG | CTG | GAG | CCG | CCT | CTC | GGG | GCC | CGA | GGA | GGG | ACC | 1344 |
| Gln | Asp | Trp | Lys | Val | Leu | Glu | Pro | Pro | Leu | Gly | Ala | Arg | Gly | Gly | Thr | |
| | | 435 | | | | 440 | | | | | 445 | | | | | |
| CTG | GAG | CTG | CGC | CCG | CGA | TCT | CGC | TAC | CGT | TTA | CAG | CTG | CGC | GCC | AGG | 1392 |
| Leu | Glu | Leu | Arg | Pro | Arg | Ser | Arg | Tyr | Arg | Leu | Gln | Leu | Arg | Ala | Arg | |
| | 450 | | | | | 455 | | | | | 460 | | | | | |
| CTC | AAC | GGC | CCC | ACC | TAC | CAA | GGT | CCC | TGG | AGC | TCG | TGG | TCG | GAC | CCA | 1440 |
| Leu | Asn | Gly | Pro | Thr | Tyr | Gln | Gly | Pro | Trp | Ser | Ser | Trp | Ser | Asp | Pro | |
| 465 | | | | | 470 | | | | | 475 | | | | | 480 | |
| ACT | AGG | GTG | GAG | ACC | GCC | ACC | GAG | ACC | GCC | TGG | ATC | TCC | TTG | GTG | ACC | 1488 |
| Thr | Arg | Val | Glu | Thr | Ala | Thr | Glu | Thr | Ala | Trp | Ile | Ser | Leu | Val | Thr | |
| | | | | 485 | | | | | 490 | | | | | 495 | | |
| GCT | CTG | CAT | CTA | GTG | CTG | GGC | CTC | AGC | GCC | GTC | CTG | GGC | CTG | CTG | CTG | 1536 |
| Ala | Leu | His | Leu | Val | Leu | Gly | Leu | Ser | Ala | Val | Leu | Gly | Leu | Leu | Leu | |
| | | | 500 | | | | | 505 | | | | | 510 | | | |
| CTG | AGG | TGG | CAG | TTT | CCT | GCA | CAC | TAC | AGG | AGA | CTG | AGG | CAT | GCC | CTG | 1584 |
| Leu | Arg | Trp | Gln | Phe | Pro | Ala | His | Tyr | Arg | Arg | Leu | Arg | His | Ala | Leu | |
| | | 515 | | | | | 520 | | | | | 525 | | | | |
| TGG | CCC | TCA | CTT | CCA | GAC | CTG | CAC | CGG | GTC | CTA | GGC | CAG | TAC | CTT | AGG | 1632 |
| Trp | Pro | Ser | Leu | Pro | Asp | Leu | His | Arg | Val | Leu | Gly | Gln | Tyr | Leu | Arg | |
| | 530 | | | | | 535 | | | | | 540 | | | | | |
| GAC | ACT | GCA | GCC | CTG | AGC | CCG | CCC | AAG | GCC | ACA | GTC | TCA | GAT | ACC | TGT | 1680 |
| Asp | Thr | Ala | Ala | Leu | Ser | Pro | Pro | Lys | Ala | Thr | Val | Ser | Asp | Thr | Cys | |
| 545 | | | | | 550 | | | | | 555 | | | | | 560 | |
| GAA | GAA | GTG | GAA | CCC | AGC | CTC | CTT | GAA | ATC | CTC | CCC | AAG | TCC | TCA | GAG | 1728 |
| Glu | Glu | Val | Glu | Pro | Ser | Leu | Leu | Glu | Ile | Leu | Pro | Lys | Ser | Ser | Glu | |
| | | | | 565 | | | | | 570 | | | | | 575 | | |
| AGG | ACT | CCT | TTG | CCC | CTG | TGT | TCC | TCC | CAG | GCC | CAG | ATG | GAC | TAC | CGA | 1776 |
| Arg | Thr | Pro | Leu | Pro | Leu | Cys | Ser | Ser | Gln | Ala | Gln | Met | Asp | Tyr | Arg | |
| | | | 580 | | | | | 585 | | | | | 590 | | | |
| AGA | TTG | CAG | CCT | TCT | TGC | CTG | GGG | ACC | ATG | CCC | CTG | TCT | GTG | TGC | CCA | 1824 |
| Arg | Leu | Gln | Pro | Ser | Cys | Leu | Gly | Thr | Met | Pro | Leu | Ser | Val | Cys | Pro | |
| | | 595 | | | | | 600 | | | | | 605 | | | | |
| CCC | ATG | GCT | GAG | TCA | GGG | TCC | TGC | TGT | ACC | ACC | CAC | ATT | GCC | AAC | CAT | 1872 |
| Pro | Met | Ala | Glu | Ser | Gly | Ser | Cys | Cys | Thr | Thr | His | Ile | Ala | Asn | His | |
| | 610 | | | | | 615 | | | | | 620 | | | | | |
| TCC | TAC | CTA | CCA | CTA | AGC | TAT | TGG | CAG | CAG | CCT | TG | | | | | 1907 |
| Ser | Tyr | Leu | Pro | Leu | Ser | Tyr | Trp | Gln | Gln | Pro | | | | | | |
| 625 | | | | | 630 | | | | | 635 | | | | | | |

( 2 ) INFORMATION FOR SEQ ID NO:4:

( i ) SEQUENCE CHARACTERISTICS:
        ( A ) LENGTH: 635 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Met | Pro | Ser | Trp | Ala | Leu | Phe | Met | Val | Thr | Ser | Cys | Leu | Leu | Ala |
| 1 | | | | 5 | | | | | 10 | | | | | 15 |
| Pro | Gln | Asn | Leu | Ala | Gln | Val | Ser | Ser | Gln | Asp | Val | Ser | Leu | Ala |

|     |     |     | 20  |     |     |     |     | 25  |     |     |     |     | 30  |     |     |
|-----|-----|-----|-----|-----|-----|-----|-----|-----|-----|-----|-----|-----|-----|-----|-----|
| Ser | Asp | Ser | Glu | Pro | Leu | Lys | Cys | Phe | Ser | Arg | Thr | Phe | Glu | Asp | Leu |
|     |     | 35  |     |     |     |     | 40  |     |     |     |     | 45  |     |     |     |
| Thr | Cys | Phe | Trp | Asp | Glu | Glu | Ala | Ala | Pro | Ser | Gly | Thr | Tyr | Gln |     |
|     | 50  |     |     |     | 55  |     |     |     |     | 60  |     |     |     |     |     |
| Leu | Leu | Tyr | Ala | Tyr | Pro | Arg | Glu | Lys | Pro | Arg | Ala | Cys | Pro | Leu | Ser |
| 65  |     |     |     |     | 70  |     |     |     |     | 75  |     |     |     |     | 80  |
| Ser | Gln | Ser | Met | Pro | His | Phe | Gly | Thr | Arg | Tyr | Val | Cys | Gln | Phe | Pro |
|     |     |     |     | 85  |     |     |     |     | 90  |     |     |     |     | 95  |     |
| Asp | Gln | Glu | Glu | Val | Arg | Leu | Phe | Phe | Pro | Leu | His | Leu | Trp | Val | Lys |
|     |     |     | 100 |     |     |     |     | 105 |     |     |     |     | 110 |     |     |
| Asn | Val | Phe | Leu | Asn | Gln | Thr | Arg | Thr | Gln | Arg | Val | Leu | Phe | Val | Asp |
|     |     | 115 |     |     |     |     | 120 |     |     |     |     | 125 |     |     |     |
| Ser | Val | Gly | Leu | Pro | Ala | Pro | Ser | Ile | Ile | Lys | Ala | Met | Gly | Gly |     |
|     | 130 |     |     |     |     | 135 |     |     |     |     | 140 |     |     |     |     |
| Ser | Gln | Pro | Gly | Glu | Leu | Gln | Ile | Ser | Trp | Glu | Glu | Pro | Ala | Pro | Glu |
| 145 |     |     |     |     | 150 |     |     |     |     | 155 |     |     |     |     | 160 |
| Ile | Ser | Asp | Phe | Leu | Arg | Tyr | Glu | Leu | Arg | Tyr | Gly | Pro | Arg | Asp | Pro |
|     |     |     |     | 165 |     |     |     |     | 170 |     |     |     |     | 175 |     |
| Lys | Asn | Ser | Thr | Gly | Pro | Thr | Val | Ile | Gln | Leu | Ile | Ala | Thr | Glu | Thr |
|     |     |     | 180 |     |     |     |     | 185 |     |     |     |     | 190 |     |     |
| Cys | Cys | Pro | Ala | Leu | Gln | Arg | Pro | His | Ser | Ala | Ser | Ala | Leu | Asp | Gln |
|     |     | 195 |     |     |     |     | 200 |     |     |     |     | 205 |     |     |     |
| Ser | Pro | Cys | Ala | Gln | Pro | Thr | Met | Pro | Trp | Gln | Asp | Gly | Pro | Lys | Gln |
|     | 210 |     |     |     |     | 215 |     |     |     |     | 220 |     |     |     |     |
| Thr | Ser | Pro | Ser | Arg | Glu | Ala | Ser | Ala | Leu | Thr | Ala | Glu | Gly | Gly | Ser |
| 225 |     |     |     |     | 230 |     |     |     |     | 235 |     |     |     |     | 240 |
| Cys | Leu | Ile | Ser | Gly | Leu | Gln | Pro | Gly | Asn | Ser | Tyr | Trp | Leu | Gln | Leu |
|     |     |     |     | 245 |     |     |     |     | 250 |     |     |     |     | 255 |     |
| Arg | Ser | Glu | Pro | Asp | Gly | Ile | Ser | Leu | Gly | Gly | Ser | Trp | Gly | Ser | Trp |
|     |     |     | 260 |     |     |     |     | 265 |     |     |     |     | 270 |     |     |
| Ser | Leu | Pro | Val | Thr | Val | Asp | Leu | Pro | Gly | Asp | Ala | Val | Ala | Leu | Gly |
|     |     | 275 |     |     |     |     | 280 |     |     |     |     | 285 |     |     |     |
| Leu | Gln | Cys | Phe | Thr | Leu | Asp | Leu | Lys | Asn | Val | Thr | Cys | Gln | Trp | Gln |
|     | 290 |     |     |     |     | 295 |     |     |     |     | 300 |     |     |     |     |
| Gln | Gln | Asp | His | Ala | Ser | Ser | Gln | Gly | Phe | Phe | Tyr | His | Ser | Arg | Ala |
| 305 |     |     |     |     | 310 |     |     |     |     | 315 |     |     |     |     | 320 |
| Arg | Cys | Cys | Pro | Arg | Asp | Arg | Tyr | Pro | Ile | Trp | Glu | Asn | Cys | Glu | Glu |
|     |     |     |     | 325 |     |     |     |     | 330 |     |     |     |     | 335 |     |
| Glu | Glu | Lys | Thr | Asn | Pro | Gly | Leu | Gln | Thr | Pro | Gln | Phe | Ser | Arg | Cys |
|     |     |     | 340 |     |     |     |     | 345 |     |     |     |     | 350 |     |     |
| His | Phe | Lys | Ser | Arg | Asn | Asp | Ser | Ile | Ile | His | Ile | Leu | Val | Glu | Val |
|     |     | 355 |     |     |     |     | 360 |     |     |     |     | 365 |     |     |     |
| Thr | Thr | Ala | Pro | Gly | Thr | Val | His | Ser | Tyr | Leu | Gly | Ser | Pro | Phe | Trp |
|     | 370 |     |     |     |     | 375 |     |     |     |     | 380 |     |     |     |     |
| Ile | His | Gln | Ala | Val | Arg | Leu | Pro | Thr | Pro | Asn | Leu | His | Trp | Arg | Glu |
| 385 |     |     |     |     | 390 |     |     |     |     | 395 |     |     |     |     | 400 |
| Ile | Ser | Ser | Gly | His | Leu | Glu | Leu | Glu | Trp | Gln | His | Pro | Ser | Ser | Trp |
|     |     |     |     | 405 |     |     |     |     | 410 |     |     |     |     | 415 |     |
| Ala | Ala | Gln | Glu | Thr | Cys | Tyr | Gln | Leu | Arg | Tyr | Thr | Gly | Glu | Gly | His |
|     |     |     | 420 |     |     |     |     | 425 |     |     |     |     | 430 |     |     |
| Gln | Asp | Trp | Lys | Val | Leu | Glu | Pro | Pro | Leu | Gly | Ala | Arg | Gly | Gly | Thr |
|     |     | 435 |     |     |     |     | 440 |     |     |     |     | 445 |     |     |     |

| Leu | Glu | Leu | Arg | Pro | Arg | Ser | Arg | Tyr | Arg | Leu | Gln | Leu | Arg | Ala | Arg |
|-----|-----|-----|-----|-----|-----|-----|-----|-----|-----|-----|-----|-----|-----|-----|-----|
|     | 450 |     |     |     |     | 455 |     |     |     |     | 460 |     |     |     |     |

| Leu | Asn | Gly | Pro | Thr | Tyr | Gln | Gly | Pro | Trp | Ser | Ser | Trp | Ser | Asp | Pro |
|-----|-----|-----|-----|-----|-----|-----|-----|-----|-----|-----|-----|-----|-----|-----|-----|
| 465 |     |     |     |     | 470 |     |     |     |     | 475 |     |     |     |     | 480 |

| Thr | Arg | Val | Glu | Thr | Ala | Thr | Glu | Thr | Ala | Trp | Ile | Ser | Leu | Val | Thr |
|-----|-----|-----|-----|-----|-----|-----|-----|-----|-----|-----|-----|-----|-----|-----|-----|
|     |     |     |     | 485 |     |     |     |     | 490 |     |     |     |     | 495 |     |

| Ala | Leu | His | Leu | Val | Leu | Gly | Leu | Ser | Ala | Val | Leu | Gly | Leu | Leu | Leu |
|-----|-----|-----|-----|-----|-----|-----|-----|-----|-----|-----|-----|-----|-----|-----|-----|
|     |     |     | 500 |     |     |     |     | 505 |     |     |     |     | 510 |     |     |

| Leu | Arg | Trp | Gln | Phe | Pro | Ala | His | Tyr | Arg | Arg | Leu | Arg | His | Ala | Leu |
|-----|-----|-----|-----|-----|-----|-----|-----|-----|-----|-----|-----|-----|-----|-----|-----|
|     |     | 515 |     |     |     |     | 520 |     |     |     |     | 525 |     |     |     |

| Trp | Pro | Ser | Leu | Pro | Asp | Leu | His | Arg | Val | Leu | Gly | Gln | Tyr | Leu | Arg |
|-----|-----|-----|-----|-----|-----|-----|-----|-----|-----|-----|-----|-----|-----|-----|-----|
|     | 530 |     |     |     |     | 535 |     |     |     |     | 540 |     |     |     |     |

| Asp | Thr | Ala | Ala | Leu | Ser | Pro | Pro | Lys | Ala | Thr | Val | Ser | Asp | Thr | Cys |
|-----|-----|-----|-----|-----|-----|-----|-----|-----|-----|-----|-----|-----|-----|-----|-----|
| 545 |     |     |     |     | 550 |     |     |     |     | 555 |     |     |     |     | 560 |

| Glu | Glu | Val | Glu | Pro | Ser | Leu | Leu | Glu | Ile | Leu | Pro | Lys | Ser | Ser | Glu |
|-----|-----|-----|-----|-----|-----|-----|-----|-----|-----|-----|-----|-----|-----|-----|-----|
|     |     |     |     | 565 |     |     |     |     | 570 |     |     |     |     | 575 |     |

| Arg | Thr | Pro | Leu | Pro | Leu | Cys | Ser | Ser | Gln | Ala | Gln | Met | Asp | Tyr | Arg |
|-----|-----|-----|-----|-----|-----|-----|-----|-----|-----|-----|-----|-----|-----|-----|-----|
|     |     |     | 580 |     |     |     |     | 585 |     |     |     |     | 590 |     |     |

| Arg | Leu | Gln | Pro | Ser | Cys | Leu | Gly | Thr | Met | Pro | Leu | Ser | Val | Cys | Pro |
|-----|-----|-----|-----|-----|-----|-----|-----|-----|-----|-----|-----|-----|-----|-----|-----|
|     |     | 595 |     |     |     |     | 600 |     |     |     |     | 605 |     |     |     |

| Pro | Met | Ala | Glu | Ser | Gly | Ser | Cys | Cys | Thr | Thr | His | Ile | Ala | Asn | His |
|-----|-----|-----|-----|-----|-----|-----|-----|-----|-----|-----|-----|-----|-----|-----|-----|
|     | 610 |     |     |     |     | 615 |     |     |     |     | 620 |     |     |     |     |

| Ser | Tyr | Leu | Pro | Leu | Ser | Tyr | Trp | Gln | Gln | Pro |
|-----|-----|-----|-----|-----|-----|-----|-----|-----|-----|-----|
| 625 |     |     |     |     | 630 |     |     |     |     | 635 |

( 2 ) INFORMATION FOR SEQ ID NO:5:

( i ) SEQUENCE CHARACTERISTICS:
        ( A ) LENGTH: 36 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:5:

TACAAGCTTG CCGTCATCAT GCCCTCTTGG GCCCTC     36

( 2 ) INFORMATION FOR SEQ ID NO:6:

( i ) SEQUENCE CHARACTERISTICS:
        ( A ) LENGTH: 33 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:6:

ACTTCTAGAC TATCAAGCAG TCTCGGAGCT GGA     33

( 2 ) INFORMATION FOR SEQ ID NO:7:

( i ) SEQUENCE CHARACTERISTICS:
        ( A ) LENGTH: 1523 base pairs
        ( B ) TYPE: nucleic acid
        ( C ) STRANDEDNESS: unknown
        ( D ) TOPOLOGY: unknown ( i i ) MOLECULE TYPE: cDNA ( i x ) FEATURE:
        ( A ) NAME/KEY: CDS
        ( B ) LOCATION: 69..1514

( x i ) SEQUENCE DESCRIPTION: SEQ ID NO:7:

```
GGATCCTCTA GAGCGGCCGC TAAGGCAGGC ACACAGTGCC GGAGAAGATG CCCTCTTGGG        60

CCCTCTTC ATG GTC ACC TCC TGC CTC CTC TTG GCC CTT CCA AAC CAG GCA         110
         Met Val Thr Ser Cys Leu Leu Leu Ala Leu Pro Asn Gln Ala
          1               5                   10

CAA GTC ACC AGC CAA GAT GTC TTC TTG CTG GCC TTG GGC ACA GAG CCC          158
Gln Val Thr Ser Gln Asp Val Phe Leu Leu Ala Leu Gly Thr Glu Pro
 15              20                  25                  30

CTG AAC TGC TTC TCC CAA ACA TTT GAG GAC CTC ACC TGC TTC TGG GAT          206
Leu Asn Cys Phe Ser Gln Thr Phe Glu Asp Leu Thr Cys Phe Trp Asp
                 35                  40                  45

GAG GAA GAG GCA GCA CCC AGT GGG ACA TAC CAG CTG CTG TAT GCC TAC          254
Glu Glu Glu Ala Ala Pro Ser Gly Thr Tyr Gln Leu Leu Tyr Ala Tyr
             50                  55                  60

CGA GGA GAG AAG CCC CGT GCA TGC CCC CTG TAT TCC CAG AGT GTG CCC          302
Arg Gly Glu Lys Pro Arg Ala Cys Pro Leu Tyr Ser Gln Ser Val Pro
                 65                  70                  75

ACC TTT GGA ACC CGG TAT GTG TGC CAG TTT CCA GCC CAG GAT GAA GTG          350
Thr Phe Gly Thr Arg Tyr Val Cys Gln Phe Pro Ala Gln Asp Glu Val
         80                  85                  90

CGC CTC TTC TTT CCG CTG CAC CTC TGG GTG AAG AAT GTG TCC CTC AAC          398
Arg Leu Phe Phe Pro Leu His Leu Trp Val Lys Asn Val Ser Leu Asn
 95                 100                 105                 110

CAG ACT TTG ATC CAG CGG GTG CTG TTT GTG GAT AGT GTG GGC CTG CCA          446
Gln Thr Leu Ile Gln Arg Val Leu Phe Val Asp Ser Val Gly Leu Pro
                115                 120                 125

GCT CCC CCC AGG GTC ATC AAG GCC AGG GGT GGG AGC CAA CCA GGG GAA          494
Ala Pro Pro Arg Val Ile Lys Ala Arg Gly Gly Ser Gln Pro Gly Glu
                130                 135                 140

CTT CAG ATC CAC TGG GAG GCC CCT GCT CCT GAA ATC AGT GAC TTC CTG          542
Leu Gln Ile His Trp Glu Ala Pro Ala Pro Glu Ile Ser Asp Phe Leu
        145                 150                 155

AGG CAT GAA CTC CGC TAT GGC CCC ACG GAT TCC AGC AAC GCC ACT GCC          590
Arg His Glu Leu Arg Tyr Gly Pro Thr Asp Ser Ser Asn Ala Thr Ala
160                 165                 170

CCC TCC GTC ATT CAG CTG CTC TCC ACA GAA ACC TGC TGC CCC ACT TTG          638
Pro Ser Val Ile Gln Leu Leu Ser Thr Glu Thr Cys Cys Pro Thr Leu
175                 180                 185                 190

TGG ATG CCG AAC CCA GTC CCT GTT CTT GAC CAG CCT CCG TGT GTT CAT          686
Trp Met Pro Asn Pro Val Pro Val Leu Asp Gln Pro Pro Cys Val His
                195                 200                 205

CCG ACA GCA TCC CAA CCG CAT GGA CCA GTG AGG ACC TCC CCA GCT GGA          734
Pro Thr Ala Ser Gln Pro His Gly Pro Val Arg Thr Ser Pro Ala Gly
                210                 215                 220

GAA GCT CCA TTT CTG ACA GTG AAG GGT GGA AGC TGT CTC GTC TCA GGC          782
Glu Ala Pro Phe Leu Thr Val Lys Gly Gly Ser Cys Leu Val Ser Gly
                225                 230                 235

CTC CAG GCT AGC AAA TCC TAC TGG CTC CAG CTA CGC AGC CAA CCC GAC          830
Leu Gln Ala Ser Lys Ser Tyr Trp Leu Gln Leu Arg Ser Gln Pro Asp
        240                 245                 250

GGG GTC TCT CTT CGT GGC TCC TGG GGA CCC TGG TCC TTC CCT GTG ACT          878
Gly Val Ser Leu Arg Gly Ser Trp Gly Pro Trp Ser Phe Pro Val Thr
255                 260                 265                 270

GTG GAT CTT CCA GGA GAT GCA GTG ACA ATT GGA CTT CAG TGC TTT ACC          926
Val Asp Leu Pro Gly Asp Ala Val Thr Ile Gly Leu Gln Cys Phe Thr
                275                 280                 285

TTG GAT CTG AAG ATG GTC ACC TGC CAG TGG CAG CAA CAA GAC CGC ACT          974
Leu Asp Leu Lys Met Val Thr Cys Gln Trp Gln Gln Gln Asp Arg Thr
                290                 295                 300
```

| | | | | | | | | | | | | | | | | |
|---|---|---|---|---|---|---|---|---|---|---|---|---|---|---|---|---|
| AGC | TCC | CAA | GGC | TTC | TTC | CGT | CAC | AGC | AGG | ACG | AGG | TGC | TGC | CCC | ACA | 1022 |
| Ser | Ser | Gln | Gly | Phe | Phe | Arg | His | Ser | Arg | Thr | Arg | Cys | Cys | Pro | Thr | |
| | | 305 | | | | | 310 | | | | | 315 | | | | |
| GAC | AGG | GAC | CCC | ACC | TGG | GAG | AAA | TGT | GAA | GAG | GAG | GAA | CCG | CGT | CCA | 1070 |
| Asp | Arg | Asp | Pro | Thr | Trp | Glu | Lys | Cys | Glu | Glu | Glu | Glu | Pro | Arg | Pro | |
| | 320 | | | | | 325 | | | | | 330 | | | | | |
| GGA | TCA | CAG | CCC | GCT | CTC | GTC | TCC | CGC | TGC | CAC | TTC | AAG | TCA | CGA | AAT | 1118 |
| Gly | Ser | Gln | Pro | Ala | Leu | Val | Ser | Arg | Cys | His | Phe | Lys | Ser | Arg | Asn | |
| 335 | | | | | 340 | | | | | 345 | | | | | 350 | |
| GAC | AGT | GTT | ATT | CAC | ATC | CTT | GTA | GAG | GTG | ACC | ACA | GCG | CAA | GGT | GCC | 1166 |
| Asp | Ser | Val | Ile | His | Ile | Leu | Val | Glu | Val | Thr | Thr | Ala | Gln | Gly | Ala | |
| | | | | 355 | | | | | 360 | | | | | 365 | | |
| GTT | CAC | AGC | TAC | CTG | GGC | TCC | CCT | TTT | TGG | ATC | CAC | CAG | GCT | GTG | CTC | 1214 |
| Val | His | Ser | Tyr | Leu | Gly | Ser | Pro | Phe | Trp | Ile | His | Gln | Ala | Val | Leu | |
| | | | 370 | | | | | 375 | | | | | 380 | | | |
| CTT | CCC | ACC | CCG | AGC | CTG | CAC | TGG | AGG | GAG | GTC | TCA | AGT | GGA | AGG | CTG | 1262 |
| Leu | Pro | Thr | Pro | Ser | Leu | His | Trp | Arg | Glu | Val | Ser | Ser | Gly | Arg | Leu | |
| | | 385 | | | | | 390 | | | | | 395 | | | | |
| GAG | TTG | GAG | TGG | CAG | CAC | CAG | TCA | TCT | TGG | GCA | GCT | CAA | GAG | ACC | TGC | 1310 |
| Glu | Leu | Glu | Trp | Gln | His | Gln | Ser | Ser | Trp | Ala | Ala | Gln | Glu | Thr | Cys | |
| | 400 | | | | | 405 | | | | | 410 | | | | | |
| TAC | CAG | CTC | CGG | TAC | ACG | GGA | GAA | GGC | CGT | GAG | GAC | TGG | AAG | GTG | CTG | 1358 |
| Tyr | Gln | Leu | Arg | Tyr | Thr | Gly | Glu | Gly | Arg | Glu | Asp | Trp | Lys | Val | Leu | |
| 415 | | | | | 420 | | | | | 425 | | | | | 430 | |
| GAG | CCA | TCT | CTC | GGT | GCC | CGG | GGA | GGG | ACC | CTA | GAG | CTG | CGC | CCC | CGA | 1406 |
| Glu | Pro | Ser | Leu | Gly | Ala | Arg | Gly | Gly | Thr | Leu | Glu | Leu | Arg | Pro | Arg | |
| | | | | 435 | | | | | 440 | | | | | 445 | | |
| GCT | CGC | TAC | AGC | TTG | CAG | CTG | CGT | GCC | AGG | CTC | AAC | GGC | CCC | ACC | TAC | 1454 |
| Ala | Arg | Tyr | Ser | Leu | Gln | Leu | Arg | Ala | Arg | Leu | Asn | Gly | Pro | Thr | Tyr | |
| | | | 450 | | | | | 455 | | | | | 460 | | | |
| CAA | GGT | CCC | TGG | AGC | GCC | TGG | TCT | CCC | CCA | GCT | AGG | GTG | TCC | ACG | GGC | 1502 |
| Gln | Gly | Pro | Trp | Ser | Ala | Trp | Ser | Pro | Pro | Ala | Arg | Val | Ser | Thr | Gly | |
| | | 465 | | | | | 470 | | | | | 475 | | | | |
| TCC | GAG | ACT | GCT | TGAGTCGAC | | | | | | | | | | | | 1523 |
| Ser | Glu | Thr | Ala | | | | | | | | | | | | | |
| | 480 | | | | | | | | | | | | | | | |

( 2 ) INFORMATION FOR SEQ ID NO:8:

( i ) SEQUENCE CHARACTERISTICS:
        ( A ) LENGTH: 482 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| | | | | | | | | | | | | | | |
|---|---|---|---|---|---|---|---|---|---|---|---|---|---|---|
| Met | Val | Thr | Ser | Cys | Leu | Leu | Leu | Ala | Leu | Pro | Asn | Gln | Ala | Gln | Val |
| 1 | | | | 5 | | | | | 10 | | | | | 15 | |
| Thr | Ser | Gln | Asp | Val | Phe | Leu | Leu | Ala | Leu | Gly | Thr | Glu | Pro | Leu | Asn |
| | | | 20 | | | | | 25 | | | | 30 | | | |
| Cys | Phe | Ser | Gln | Thr | Phe | Glu | Asp | Leu | Thr | Cys | Phe | Trp | Asp | Glu | Glu |
| | | 35 | | | | | 40 | | | | | 45 | | | |
| Glu | Ala | Ala | Pro | Ser | Gly | Thr | Tyr | Gln | Leu | Leu | Tyr | Ala | Tyr | Arg | Gly |
| | 50 | | | | | 55 | | | | | 60 | | | | |
| Glu | Lys | Pro | Arg | Ala | Cys | Pro | Leu | Tyr | Ser | Gln | Ser | Val | Pro | Thr | Phe |
| 65 | | | | | 70 | | | | | 75 | | | | | 80 |
| Gly | Thr | Arg | Tyr | Val | Cys | Gln | Phe | Pro | Ala | Gln | Asp | Glu | Val | Arg | Leu |
| | | | | 85 | | | | | 90 | | | | | 95 | |
| Phe | Phe | Pro | Leu | His | Leu | Trp | Val | Lys | Asn | Val | Ser | Leu | Asn | Gln | Thr |

|   |   |   | | | 100 | | | | | 105 | | | | | 110 |
|---|---|---|---|---|---|---|---|---|---|---|---|---|---|---|---|

Leu Ile Gln Arg Val Leu Phe Val Asp Ser Val Gly Leu Pro Ala Pro
          115              120              125

Pro Arg Val Ile Lys Ala Arg Gly Gly Ser Gln Pro Gly Glu Leu Gln
    130              135              140

Ile His Trp Glu Ala Pro Ala Pro Glu Ile Ser Asp Phe Leu Arg His
145              150              155              160

Glu Leu Arg Tyr Gly Pro Thr Asp Ser Ser Asn Ala Thr Ala Pro Ser
              165              170              175

Val Ile Gln Leu Leu Ser Thr Glu Thr Cys Cys Pro Thr Leu Trp Met
          180              185              190

Pro Asn Pro Val Pro Val Leu Asp Gln Pro Pro Cys Val His Pro Thr
        195              200              205

Ala Ser Gln Pro His Gly Pro Val Arg Thr Ser Pro Ala Gly Glu Ala
    210              215              220

Pro Phe Leu Thr Val Lys Gly Gly Ser Cys Leu Val Ser Gly Leu Gln
225              230              235              240

Ala Ser Lys Ser Tyr Trp Leu Gln Leu Arg Ser Gln Pro Asp Gly Val
              245              250              255

Ser Leu Arg Gly Ser Trp Gly Pro Trp Ser Phe Pro Val Thr Val Asp
            260              265              270

Leu Pro Gly Asp Ala Val Thr Ile Gly Leu Gln Cys Phe Thr Leu Asp
        275              280              285

Leu Lys Met Val Thr Cys Gln Trp Gln Gln Gln Asp Arg Thr Ser Ser
        290              295              300

Gln Gly Phe Phe Arg His Ser Arg Thr Arg Cys Cys Pro Thr Asp Arg
305              310              315              320

Asp Pro Thr Trp Glu Lys Cys Glu Glu Glu Pro Arg Pro Gly Ser
                325              330              335

Gln Pro Ala Leu Val Ser Arg Cys His Phe Lys Ser Arg Asn Asp Ser
        340              345              350

Val Ile His Ile Leu Val Glu Val Thr Thr Ala Gln Gly Ala Val His
        355              360              365

Ser Tyr Leu Gly Ser Pro Phe Trp Ile His Gln Ala Val Leu Leu Pro
    370              375              380

Thr Pro Ser Leu His Trp Arg Glu Val Ser Ser Gly Arg Leu Glu Leu
385              390              395              400

Glu Trp Gln His Gln Ser Ser Trp Ala Ala Gln Glu Thr Cys Tyr Gln
            405              410              415

Leu Arg Tyr Thr Gly Glu Gly Arg Glu Asp Trp Lys Val Leu Glu Pro
        420              425              430

Ser Leu Gly Ala Arg Gly Gly Thr Leu Glu Leu Arg Pro Arg Ala Arg
    435              440              445

Tyr Ser Leu Gln Leu Arg Ala Arg Leu Asn Gly Pro Thr Tyr Gln Gly
    450              455              460

Pro Trp Ser Ala Trp Ser Pro Pro Ala Arg Val Ser Thr Gly Ser Glu
465              470              475              480

Thr Ala